US007981915B2

(12) United States Patent
Freedman

(10) Patent No.: US 7,981,915 B2
(45) Date of Patent: Jul. 19, 2011

(54) METHODS FOR MODULATING PPAR BIOLOGICAL ACTIVITY FOR THE TREATMENT OF DISEASES CAUSED BY MUTATIONS IN THE CFTR GENE

(75) Inventor: Steven D. Freedman, Chestnut Hill, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 1080 days.

(21) Appl. No.: 11/262,645

(22) Filed: Oct. 31, 2005

(65) Prior Publication Data

US 2006/0160867 A1 Jul. 20, 2006

Related U.S. Application Data

(63) Continuation-in-part of application No. PCT/US2004/013412, filed on Apr. 30, 2004.

(60) Provisional application No. 60/466,672, filed on Apr. 30, 2003.

(51) Int. Cl.
*A61K 31/415* (2006.01)
*A61K 31/335* (2006.01)
*A61K 31/34* (2006.01)
*A61K 31/195* (2006.01)
*A61K 31/19* (2006.01)
*A61K 31/08* (2006.01)

(52) U.S. Cl. ........ 514/396; 514/458; 514/474; 514/561; 514/562; 514/570; 514/722

(58) Field of Classification Search .................. 514/369, 514/458, 474, 561, 562, 570, 722
See application file for complete search history.

(56) References Cited

U.S. PATENT DOCUMENTS

| | | | |
|---|---|---|---|
| 5,436,269 | A | 7/1995 | Yazawa et al. |
| 5,925,657 | A | 7/1999 | Seed et al. |
| 5,993,221 | A | 11/1999 | Bistrian |
| 6,180,671 | B1 | 1/2001 | Freedman et al. |
| 6,384,065 | B1 | 5/2002 | Chaki et al. |
| 6,492,425 | B1 | 12/2002 | Callahan et al. |
| 6,525,083 | B2 | 2/2003 | Acton, III et al. |
| 6,552,081 | B1 | 4/2003 | Freedman et al. |
| 2003/0186215 | A1 | 10/2003 | Kishimoto et al. |
| 2005/0101581 | A1 | 5/2005 | Reading et al. |
| 2005/0134859 | A1* | 6/2005 | Kalayeh et al. ............... 356/437 |
| 2006/0127491 | A1 | 6/2006 | Puder et al. |
| 2010/0256235 | A1 | 10/2010 | Puder et al. |

FOREIGN PATENT DOCUMENTS

| EP | 0682878 A2 | 11/1995 |
|---|---|---|
| EP | 1133294 B1 | 8/2010 |

OTHER PUBLICATIONS

Chambrier et al., "Eicosapentaenoic Acid Induces mRNA Expression of Peroxisome Proliferator-Activated Receptor γ," *Obes. Res.* 10(6):518-525 (2002).

Davies et al., "Unique Ability of Troglitazone to Up-Regulate Peroxisome Proliferator-Activated Receptor-γ Expression in Hepatocytes," *J. Pharmacol. Exp. Ther.* 300(1):72-77 (2002).
De Vizia et al., "Effect of an 8-Month Treatment with Omega-3 Fatty Acids (Eicosapentaenoic and Docosahexaenoic) in Patients with Cystic Fibrosis," *J. Parenter. Enteral. Nutr.* 27(1):52-57 (2003) (abstract only).
de Vries et al., "Haplotype Identity Between Individuals Who Share a CFTR Mutation Allele 'Identical by Descent': Demonstration of the Usefulness of the Haplotype-Sharing Concept for Gene Mapping in Real Populations," *Human Genetics* 98(3):304-309 (1996).
de Vries et al., "Haplotype Identity Between Individuals Who Share a CFTR Mutation Allele Identical by Descent: Demonstration of the Usefulness of the Haplotype Sharing Concept for Gene Mapping in Real Populations," Chapter 6 (pp. 71-82) of Dissertation of de Vries, "Application of Molecular Techniques in Population Genetic Studies of Cystic Fibrosis in the Netherlands," Rijksuniveriteit Groningen (1996).
Dubuquoy et al., "Role of Peroxisome Proliferator-Activated Receptor γ and Retinoid X Receptor Heterodimer in Hepatogastroenterological Diseases," *Lancet* 360(9343):1410-1418 (2002).
Freedman et al., "A Membrane Lipid Imbalance Plays a Role in the Phenotypic Expression of Cystic Fibrosis in cftr$^{-/-}$ Mice," *Proc. Natl. Acad. Sci. U.S.A.* 96(24):13995-14000 (1999).
Hotson, "Mutations to the CFTR Protein," *Bioinformatics 118, Final Reports for 2000*, Stanford University (2000).
Huang et al., "The Pathophysiological Function of Peroxisome Proliferator-Activated-Receptor-γ in Lung-Related Diseases," *Respir. Res.* 6(1):102-110 (2005).
Printout from http://www.oml.gov/sci/techresources/Human_Genome/posters/chromosome/cftr.shtml "CTFR: The Gene Associated with Cystic Fibrosis" (2003), printed Aug. 9, 2007.
International Preliminary Report on Patentability for International Patent Application No. PCT/US04/13412, issued Nov. 4, 2005.
International Preliminary Report on Patentability for International Patent Application No. PCT/US06/42474, issued May 6, 2008.
International Search Report for International Patent Application No. PCT/US04/13412, mailed Oct. 29, 2004.
International Search Report for International Patent Application No. PCT/US06/42474, mailed May 10, 2007.
Naruse et al., "*CFTR* Gene Mutation and Chloride Channel Dysfunction in Chronic Pancreatitis: From Gene to Clinics?," *J. Pancreas* 2(5 Suppl.): 332 (2001).
Nguyen et al., "The PPAR Activator Docosahexaenoic Acid Prevents Acetaminophen Hepatotoxicity in Male CD-1 Mice," *Journal of Toxicology and Environmental Health, Part A* 58:171-186 (1999).
Ockenga et al., "Mutations of the Cystic Fibrosis Gene, but not Cationic Trypsinogen Gene, Are Associated with Recurrent or Chronic Idiopathic Pancreatitis," *Am. J. Gastroenterol.* 95(8):2061-2067 (2000) (abstract only).
Ollero et al., "Decreased Expression of Peroxisome Proliferator Activated Receptor Gamma in cftr$^{-/-}$ Mice," *J. Cell Physiol.* 200(2):235-244 (2004).

(Continued)

*Primary Examiner* — Raymond J Henley, III
(74) *Attorney, Agent, or Firm* — Clark & Elbing LLP; Kristina Bieker-Brady

(57) ABSTRACT

This invention features methods for treating diseases associated with mutations in the CFTR gene by administering PPAR agonists, specifically PPARγ, PPARα, and PPARδ agonists, PPAR inducers, and/or antioxidants. Also disclosed are screening methods for identifying therapeutically useful candidate compounds.

23 Claims, 19 Drawing Sheets

OTHER PUBLICATIONS

Schroeder et al., "Protection Against Bronchial Asthma by CFTR Δ F508 Mutation: A Heterozygote Advantage in Cystic Fibrosis," *Nat. Med.* 1(7):703-705 (1995) (abstract only).

Singer and Richter-Heinrich, "Stress and Fatty Liver—Possible Indications for Dietary Long-Chain n-3 Fatty Acids," Medical Hypotheses 36:90-94, (1991).

Wood et al., "Improved Antioxidant and Fatty Acid Status of Patients with Cystic Fibrosis after Antioxidant Supplementation Is Linked to Improved Lung Function," *Am. J. Clin. Nutr.* 77:150-159, (2003).

Written Opinion of the International Searching Authority for International Patent Application No. PCT/US04/13412, mailed Oct. 29, 2004.

Written Opinion o the International Searching Authority for International Patent Application No. PCT/US06/42474, mailed May 10, 2007.

\* cited by examiner

A

B

C

D

LXR protein expression by western blot analysis in macrophages

METHODS FOR MODULATING PPAR BIOLOGICAL ACTIVITY FOR THE TREATMENT OF DISEASES CAUSED BY MUTATIONS IN THE CFTR GENE

CROSS-REFERENCE TO RELATED APPLICATIONS

This application is a Continuation-in-part application of and claims priority to International Application No. PCT/US2004/013412, filed Apr. 30, 2004, which was published in English under PCT Article 21(2), and which claims the benefit of U.S. provisional application No. 60/466,672, filed Apr. 30, 2003, both of which are incorporated herein by reference in their entirety.

STATEMENT AS TO FEDERALLY SPONSORED RESEARCH

This invention was funded by grant R01 DK 52765 from the National Institute of Health. The government may have certain rights in the invention.

FIELD OF THE INVENTION

The present invention relates to the treatment of cystic fibrosis and other diseases associated with mutations in the CFTR gene.

BACKGROUND OF THE INVENTION

Approximately one in 2000 Caucasians have cystic fibrosis (CF), a genetic disorder caused by inactivating mutations in the cystic fibrosis transmembrane conductance regulator (CFTR) gene. The CFTR protein, a member of the ABC transporter family, forms a chloride channel localized to the plasma membrane. The protein consists of five domains: two membrane-spanning domains that form the chloride ion channel, two nucleotide-binding domains that hydrolyze ATP, and a regulatory domain. Expression of the CFTR gene is highest in cells that line passageways of the lungs, pancreas, colon, ileum, and genitourinary tract.

In addition to CF, defects in the CFTR gene are associated with diseases including, for example, pancreatitis, chronic obstructive pulmonary disease (COPD), asthma, chronic sinusitis, primary sclerosing cholangitis, and congenital bilateral absence of the vas deferens (CBAVD).

The most common inactivating mutation of the CFTR gene, detected in about 70% of CF patients, is a deletion of the three base pairs encoding the phenylalanine at amino acid residue 508 ($\Delta$F508). The F508 residue is located in a membrane spanning domain and its deletion causes incorrect folding of the newly synthesized protein. As a result, misfolded protein is degraded in the endoplasmic reticulum shortly after synthesis. Patients having a homozygous $\Delta$F508 deletion tend to have the most severe symptoms of cystic fibrosis, resulting from a loss of chloride ion transport. The disturbance in the sodium and chloride ion balance in the cells lining the respiratory tract results in a thick, sticky mucus layer that is not easily removed by the cilia. The altered mucus also traps bacteria, resulting in chronic infections. Accordingly, most CF therapy is directed to controlling persistent and often fatal lung infections. There is a need for improved therapies that treat the underlying causes of CF and other CFTR-related diseases.

SUMMARY OF THE INVENTION

The invention features a method for treating a disease in a human patient that has a mutation in the CFTR gene by administering to the patient a therapeutically effective amount of a peroxisome proliferator-activated receptor (PPAR) inducer, a PPAR agonist, an AP-1 inhibitor, a STAT inhibitor, an NFkB inhibitor, or an LXR agonist. PPARs generally include PPARα, PPARδ, and PPARγ. Diseases caused by mutations in a CFTR gene include, for example, cystic fibrosis, pancreatitis, chronic obstructive pulmonary disease (COPD), asthma, chronic sinusitis, primary sclerosing cholangitis, liver disease, bile duct injury, and congenital bilateral absence of the vas deferens. The diseases that are treatable by the therapeutic methods of the invention include any disease caused by any of the 1,300 or more mutations in the CFTR protein. See for example, J. Zielenski, Canadian CF registry database; Cutting et al., Nature 346:366-369, 1990; Dean et al., Cell 61:863-870, 1990; Kerem et al., Science 245:1073-1080, 1989; Kerem et al., Proc. Natl. Acad. Sci. USA 87:8447-8451, 1990; and Welsh et al., "Cystic Fibrosis," Metabolic and Molecular Basis of Inherited Disease ($8^{th}$ Ed. 2001), pp. 5121-88. Particularly amenable to treatment are diseases caused by a deletion of the phenylalanine normally present at amino acid residue 508 of the CFTR protein ($\Delta$F508). The patients being treated according to the methods of this invention may be heterozygous or homozygous for a CFTR mutation.

Useful PPAR inducers and agonists affect any PPAR, but particularly PPARγ, (e.g., PPARγ1 and PPARγ2), PPARα, and PPARδ. Examples include eicosapentaenoic acid; any of the thiazolidinediones, but particularly pioglitazone (ACtos™, Takeda Pharmaceuticals), rosiglitazone (Avandia™, GlaxoSmithKline), thioglitazone and analogs thereof; L-tyrosine derivatives such as fluoromethyloxycarbonyl; non-steroidal anti-inflammatory drugs such as indomethacin, ibuprofen, naprosyn, and fenoprofen; and anti-oxidants such as vitamin E, vitamin C, S-adenosyl methionine, selenium, idebenone, cysteine, dithioerythritol, dithionite, dithiothreitol, and pyrosulfate. Additional examples of PPARα agonists and inducers include DHA, WY14643, and any of the fibrates, particularly, fenofibrate, bezafibrate, gemfibrozil, and analogs thereof.

In one example, the method includes the use of a PPARα antagonist for the treatment of bile duct injury or cystic fibrosis liver disease associated with a mutation in a CFTR gene.

The invention also features a method for treating a disease in a human patient that has a mutation in the CFTR gene by administering to the patient a therapeutically effective amount of a PPARα agonist and a therapeutically effective amount of a PPARγ agonist, including but not limited to, the compounds described herein.

The invention also features a method for treating a disease in a human patient that has a mutation in the CFTR gene by administering to the patient a therapeutically effective amount of a dual PPARα/PPARγ agonist. Examples of dual PPARα/PPARγ agonists include muraglitazar (Bristol-Myers Squibb), tesaglitazar (AstraZeneca)), AR-HO39242 (Astra/Zeneca), GW-409544 (Glaxo-Wellcome), KRP297 (Kyorin Merck). See U.S. Pat. No. 6,414,002 for additional exemplary dual PPARα/PPARγ agonist compounds.

Useful AP-1 inhibitors include, for example, nordihydroguaiaretic acid, SP600125, SR11302, pyrrolidine dithiocarbamate, curcumin, PD98059, and the spiro compounds.

Useful STAT inhibitors include, for example, the SSI-1, SSI-2, and SSI-3 proteins. These proteins may be administered by any suitable route (e.g., inhalation, intravenous, intramuscular, or subcutaneous injection). Alternatively, they can be expressed by the target cells in the patient using gene therapy techniques. Useful STAT inhibitors include, for example, tripeptides having the sequence proline-tyrosineleucine or alanine-tyrosine-leucine, wherein said tyrosine is phosphorylated (phospho-tyrosine).

Useful NFkB inhibitor include, for example, 2-chloro-N-[3,5-di(trifluoromethyl)phenyl]-4-(trifluoromethyl)pyrimidine-5-carboxamide (SP-100030); 3,4-dihydro-4,4-dimethyl-2H-1,2-benzoselenazine (BXT-51072); declopramide (Oxi-104), dexlipotam, a salicylanilide (see, U.S. Pat. No. 6,492,425, hereby incorporated by reference), 2-hydroxy-4-trifluoromethylbenzoic (HTB) acid and its derivatives (e.g., triflsal); see U.S. Pat. No. 6,414,025, hereby incorporated by reference).

Useful LXR agonists include GX3965 and T0901317 (Cayman Chemical Co., Ann Arbor, Mich.).

The invention also features methods for identifying compounds useful for treating a disease in a patient having a mutation in the CFTR gene and wherein said mutation is associated with said disease. In one aspect, the method has the steps of: (i) providing cells that express a PPAR (e.g., PPARγ, PPARα, and PPARδ), (ii) contacting the cells with a candidate compound, and (iii) assessing the level of PPAR expression in the cells relative to the level of PPAR expression in the absence of the candidate compound, wherein a candidate compound that increases the level of PPAR expression is identified as a compound useful for treating the disease. PPAR expression may be assessed using any appropriate technique known to those skilled in the art. Techniques include, for example, western blotting and RNA analysis (e.g., northern blotting).

In another aspect, the method has the steps of: (i) providing cells that express a PPAR protein (e.g., PPARγ, PPARα, and PPARδ), (ii) contacting the cells with a candidate compound, and (iii) assessing the half life of the PPAR protein in the cells relative to the half life of the PPAR protein in the absence of the candidate compound, wherein a candidate compound that increases the half life is identified as a compound useful for treating the disease.

In another aspect, the method has the steps of: (i) providing cells that express a PPAR (e.g., PPARγ, PPARα, and PPARδ), (ii) contacting the cells with a candidate compound, and (iii) assessing the level of PPAR translocation to the nucleus of the cells relative to the level of PPAR expression in the absence of the candidate compound, wherein a candidate compound that increases the level of PPAR translocation to the nucleus is identified as a compound useful for treating the disease. Immunohistochemistry is a particularly useful method for determining PPAR nuclear translocation.

Any cells that express any PPAR (e.g., PPARγ, PPARα, and PPARδ) are useful in these screening methods, for example, pancreatic exocrine cells, lung cells, intestinal cells, bile duct cells, or macrophages. Alternatively, cells engineered to express a recombinant PPAR gene are also useful. Particularly useful PPARγ isoforms include, for example, PPARγ1 and PPARγ2.

The invention also features a method for treating a disease in a human patient that has a mutation in the CFTR gene by administering to the patient a therapeutically effective amount of an antioxidant. Antioxidants useful in the methods of this invention include, for example, vitamin E, vitamin C, S-adnenosyl methionine, selenium, beta-carotene, idebenone, cysteine, dithioerythritol, dithionite, dithiothreitol, and pyrosulfite.

Any of the therapeutic compounds of the invention can be used alone or in combination with one or more additional compounds (e.g., another compound of the invention) for the treatment methods of the invention.

By "PPAR" is meant peroxisome proliferator-activated receptor. PPARs generally serve as receptors for two classes of drugs: the hypolipidemic fibrates and the insulin sensitizing thiazolidinediones. PPARs are ligand-activated transcription factors that increase transcription of target genes by binding to a specific nucleotide sequence in the gene's promoter. The three preferred PPAR isotypes for the methods of the invention are PPARγ, PPARα, and PPARδ.

By "biological activity," when referring to PPARs (e.g., PPARγ, PPARδ, and PPARα), is meant any effect on cell physiology normally associated with the activation of this receptor. One important PPAR biological activity is its translocation to the nucleus of the cell. Other assays for PPAR biological activity are based on the ability of PPAR to bind to the RXR receptor. Alternatively, PPAR biological activity can be measured using a reporter gene operably linked to a PPAR-inducible promoter and assessing expression of the reporter gene. Biological activity can be measured using any appropriate methodology known in the art (see, for example, Kliewer et al., Proc. Natl. Acad. Sci. USA 94: 4318-4323, 1997).

By "PPAR inducer" is meant any compound that increases the biological activity or expression of one or more PPARs (e.g., PPARγ, PPARδ, and PPARα) in a cell. PPAR inducers may increase biological activity by post-transcriptionally activating PPAR. One example of a PPAR inducer is eicosapentaenoic acid.

By "PPAR agonist" is meant any compound that increases binding to one or more PPARs (e.g., PPARγ, PPARα, and PPARδ) and increases its biological activity (i.e., causes translocation of the PPAR to the nucleus). Examples of PPARγ agonists include any of the thiazolidinediones, but particularly rosiglitazone (Avandia™, GlaxoSmithKline), thioglitazone, and pioglitazone (Actos™, Takeda Pharmaceuticals), and analogs thereof. Additional examples of PPARγ agonists include non-steroidal anti-inflammatory drugs, such as indomethacin, ibuprofen, naprosyn, and fenoprofen, and antioxidants such as vitamin E, vitamin C, S-adnenosyl methionine, selenium, beta-carotene, idebenone, cysteine, dithioerythritol, dithionite, dithiothreitol, and pyrosulfite. Examples of PPARα agonists include Docosahexaenoic Acid (DHA), Wy14643, and any of the fibrates (e.g., fenafibrate, bezafibrate, gemfibrozil, and analogs thereof).

By "LXR" is meant liver X receptor (LXR) which is a member of the family of nuclear receptors that include the farnesoid X receptor, retinoic acid X receptors, and peroxisome proliferator-activated receptors. LXR is involved in the regulation of the transcription of genes involved in lipid and sterol metabolism and balance as well as the regulation of bacterial inflammatory signaling in macrophages. LXR ligands, such as GX3965 and T0901317 are currently under investigation as potential therapeutic agents for the treatment of low HDL, a disorder common in both nondiabetic and diabetic humans.

By "therapeutically effective amount" is meant an amount sufficient to provide medical benefit.

By "substantially pure," when referring to a naturally occurring compound (i.e., EPA) is meant a compound that has been partially or totally separated from the components that naturally accompany it. Typically, the compound is substantially pure when it is at least 50%, 60%, 70%, 80%, 90% 95%, or even 99%, by weight, free from the organic molecules with which it is naturally associated. For example, substantially pure EPA may be obtained by extraction from a natural source such as fish oil. Alternatively, chemical synthesis of EPA may result in a totally pure product.

BRIEF DESCRIPTION OF DRAWINGS

FIG. 7A shows an electrophoretic mobility shift assay.

FIG. 7B is a competition binding experiment using unlabled oligonucleotide. A 100-fold excess of the synthetic PPRE was used.

DETAILED DESCRIPTION

Figure 1:
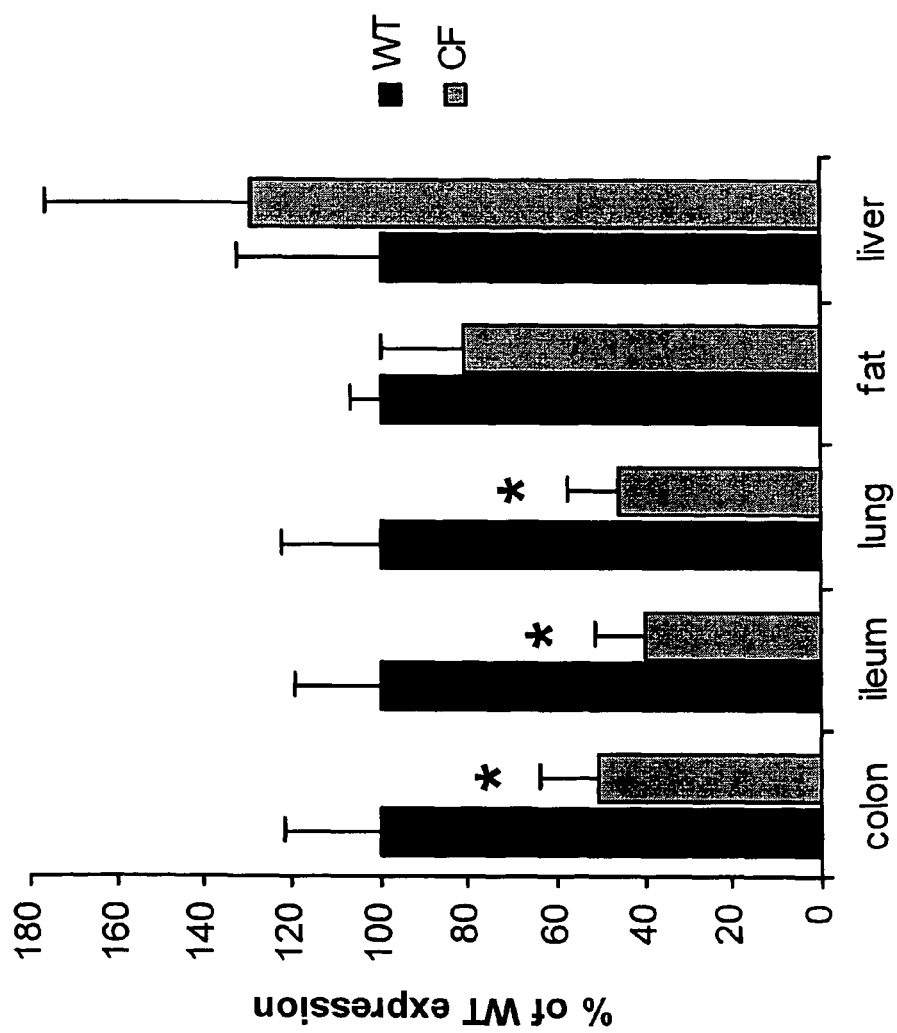
FIG. 1 is a bar graph comparing PPARγ mRNA expression levels in various tissues of cftr$^{-/-}$ and wild-type mice. mRNA expression of total PPARγ was analyzed in colon, ileum, fat, liver and lung from wild-type (WT) and cftr$^{-/-}$ (CF) mice. RNA extracts were subjected to quantitative RT-PCR. Values for cftr$^{-/-}$ tissues are expressed relative to WT, where 100% is the mean value in each of the respective tissues. Data are expressed as means±SEM (n=5). *p<0.05.

Ligands (agonists) and inducers of PPARs, particularly inducers of PPARα or PPARγ, are useful for treating diseases caused by mutations in the CFTR gene. Antioxidants, alone or in combination with PPAR ligands and inducers, are also useful for treating these diseases. Diseases amenable to treatment include, for example, cystic fibrosis (CF), pancreatitis, chronic obstructive pulmonary disease (COPD), asthma, chronic sinusitis, primary sclerosing cholangitis, bile duct injury, liver disease, and congenital bilateral absence of the vas deferens.

A fatty acid imbalance in plasma from cystic fibrosis patients and in tissues from cftr$^{-/-}$ mice has been extensively reported, first as an essential fatty acid deficiency (Farrel et al., Pediatr. Res. 19: 104-109, 1985) and more recently as an increase in arachidonic and a concomitant decrease in docosahexaenoic acids (Freedman et al., Proc. Natl. Acad. Sci. USA, 96: 13995-14000, 1999). This defect has been suggested to play a role in the increased inflammatory response in cystic fibrosis, since arachidonic acid is the precursor of a number of eicosanoids and inflammatory mediators. Both fatty acids have independent biosynthetic precursors, and although they use similar processes and share some of the enzymes involved, docosahexaenoic acid synthesis requires an additional β-oxidation step that takes place in peroxisomes. Impairment in the peroxisomal β-oxidation of docosahexaenoic acid precursors would lead to low docosahexaenoic acid and high arachidonic acid levels.

Peroxisome Proliferator-Activated Receptors

PPARs are a subfamily of ligand-activated transcription factors. They act by binding as heterodimers with a retinoid-X receptor (RXR) to specific DNA sequences known as peroxisome proliferator responsive elements (PPRE) (reviewed in Berger et al., Annu. Rev. Med., 53: 409-435, 2002). The PPAR genes were discovered in 1990, when found to be activated by peroxisome proliferators. The three PPAR genes most relevant to this invention are PPARγ, PPARα, and PPARδ. PPARγ has two isoforms, 1 and 2. PPARγ2 is mostly expressed in adipose tissue while PPARγ1 is more widely distributed including small and large intestine. PPARα is present in hepatocytes, macrophages, and monocytes and is activated by polyunsaturated fatty acids and fibrates.

PPARs are involved in the regulation of lipid metabolism, by regulating the expression of a number of genes, such as the fatty acid-binding protein aP, phosphoenolpyruvate carboxykinase, acyl-CoA synthase, lipoprotein lipase, the fatty acid transport protein-1, CD36, and leptin. In general, PPARγ activation augments lipid catabolism and induces differentiation of fibroblasts into adipocytes. PPAR-γ also regulates peroxisomal proliferation and lipid metabolism by increasing beta oxidation. Because DHA is synthesized in peroxisomes by beta oxidation, PPAR inducers increase DHA levels in cells, attenuating or reversing the effects of CFTR deletions.

PPARα is activated by free fatty acids including linoleic, arachidonic, and oleic acids. Induction of peroxisomes by this mechanism leads to a reduction in blood triglyceride levels.

PPARγ and PPARα are also involved in the regulation of inflammatory responses and the enhancement of insulin sensitivity. PPARγ and PPARα have also been shown to regulate cell proliferation and cell differentiation and PPARα has been shown to suppress apoptosis in hepatocytes.

PPAR agonists, specifically PPARγ and PPARα agonists, are used as insulin sensitizers and regulators of lipid homeostasis in the treatment of diabetes. PPARγ and PPARα agonists also inhibit the expression of the proinflammatory and insulin resistance-inducing cytokine TNFα, increase other insulin signaling mediators, and block the NF-kB proinflammatory signaling pathway PPARγ has been shown to exert anti-inflammatory effects in the colon. For example, fibrates, which are PPARα agonists, may be of benefit in the treatment of atherosclerotic disease not by decreasing serum lipids, but rather by increasing cholesterol metabolism in foamy macrophages and decreasing inflammation and ulcerations within atherosclerotic plaques through PPARα pathways. In another example, the PPARγ synthetic agonists thiazolidinediones (TZDs) have been used as anti-diabetic drugs and exert anti-inflammatory effects in the colon.

Modulating PPAR Biological Activity for the Treatment of Diseases Caused by Mutations in the CFTR Gene The results of the experiments described in the examples below demonstrate that PPARγ mRNA expression is decreased in those tissues specifically regulated by CFTR (colon, ileum, liver, and lung). This was confirmed at the protein level by western blot analysis of colon. Based on immunohistochemistry, the proportion of PPARγ-expressing cells was not decreased in these particular cystic fibrosis tissues from cftr$^{-/-}$ mice and hence would not explain the lower levels of PPARγ. The fact that no significant differences were found in liver or fat where CFTR RNA levels were found to be extremely low, suggests that CFTR may play a role in modulating PPARγ expression. It should be pointed out that although there is expression of CFTR in bile ducts, these cells represent less than 3% of total cells in the liver.

The results of western blotting and immunohistochemistry also show that the subcellular localization of PPARγ is altered in cftr$^{-/-}$ mice. This alteration consists of a shift from predominantly nuclear staining in wild-type animals to a diffuse cytoplasmic staining in cftr$^{-/-}$ mice. Western blot analysis of colonic mucosal scrapings demonstrated that this is mostly due to a decrease in the nuclear presence of PPARγ, and was supported by the decreased binding of the PPARγ/RXR complex to PPRE in cftr$^{-/-}$ colon, as revealed by EMSA. This confirms that not only expression of PPARγ, but also its function as a transcription factor is compromised in cftr$^{-/-}$ tissues. The fact that administration of rosiglitazone, a PPAR ligand, restored both the nuclear localization of PPARγ in ileum and colon based on immunohistochemistry, and binding to PPRE in colon cells as shown by EMSA, indicates that activation followed by translocation to the nucleus can occur in cftr$^{-/-}$ mice.

PPARγ has been shown to be expressed in multiple tissues. Adipose tissue and colon are the major organs expressing PPARγ, while lower levels are present in kidney, liver, skin, ileum and mononuclear blood cells (Dubuquoy et al., Lancet 360: 1410-1418, 2002). PPARγ2 mRNA is predominantly expressed in adipocytes with less significant amounts in liver, while PPARγ1 mRNA is more universally distributed including small and large intestine, kidney, muscle and liver (Fajas et al., J. Biol. Chem. 272: 18779-18789, 1997). Lower but detectable expression levels of PPARγ1 have also been reported in both mouse and human lung tissue (Lambe et al., Eur. J. Biochem. 239: 1-7, 1996; Zhu et al., J. Biol. Chem. 268: 26817-26820, 1993). Expression in lung has been localized in alveolar type-II pneumocytes whereas receptor activity has been found in human airway epithelial cells, as well as in several human lung epithelial cell lines. These results are in agreement with the immunohistochemical results seen in the experiments described below.

The mechanism by which PPARγ expression is decreased in these select CFTR expressing tissues in cftr$^{-/-}$ mice may be due to either (i) a reduction in transcription and translation of PPARγ, (ii) shorter half life of the protein, or (iii) a lack of stimulation by endogenous PPARγ ligands. Different ligands show diverse effects on PPARγ mRNA expression. Only troglitazone, unlike rosiglitazone and other high affinity PPARγ ligands, has been shown to upregulate PPARγ expression in nonadipose tissues and cell lines (Davies et al., Mol. Cell. Biol. Res. Commun. 2: 202-208, 1999; J. Pharmacol. Exp. Ther. 300: 72-77, 2002). The experiments below demonstrate that rosiglitazone induces nuclear translocation of PPARγ but did not increase RNA expression is in agreement with these findings. The mechanism for troglitazone-induced RNA expression of PPARγ may occur through its antioxidant potential, since α-tocopherol shows a similar effect.

In contrast to PPARγ, where there is low basal levels in epithelial cells in affected organs from the cftr$^{-/-}$ mouse, the experiments described in Examples 7-9, below, demonstrate the lack of induction of PPARα in inflammatory diseases in the cftr$^{-/-}$ mouse model leading to a pro-inflammatory state. Comparing peritoneal macrophages from cftr$^{-/-}$ mice to those from wild-type littermates, there is a lack of induction of PPARα (based on electrophorectic mobility gel shift assays) in the CF macrophages, resulting in an increase in NFκB, TNF, and IL-6. In another set of experiments, also described below, it was demonstrated that in the liver of wild-type mice, colitis leads to an induction of PPARα, which prevents bile duct inflammation. In cftr$^{-/-}$ mice, there is no increase in PPARα at the RNA or protein level resulting in bile duct inflammation as evidenced by increased mononuclear cell infiltrates around the bile ducts and bile duct proliferation.

PPAR activation has been shown to result in decreased inflammation through inhibition of AP-1, STAT and NFkB pathways in monocytes and macrophages that results in a modulatory effect on cytokine secretion (Jiang et al., Nature 391: 82-86, 1998; Nagy et al., Cell 93: 229-240, 1998; Ricote et al., Nature 391: 79-82, 1998), inhibition of IL-2 secretion from T cells (Clark et al., J. Immunol. 164: 1364-1371, 2000), and inhibition of NFkB activity in epithelial cells (Su et al., J. Clin. Invest. 104: 383-389, 1999). Thus, a decrease in PPAR expression and function could explain several sequelae that are associated with the cystic fibrosis phenotype such as an excessive host inflammatory response, increased peripheral insulin resistance, and alterations in lipid metabolism within the peroxisomal compartment.

Cystic fibrosis is also associated with a high incidence of impaired glucose tolerance and development of diabetes mellitus. A combination of decreased insulin secretion and increased insulin resistance has been proposed. The former is attributed to pancreatic atrophy and fibrosis characteristic of cystic fibrosis patients, affecting both exocrine and endocrine function. The latter effect on increased peripheral insulin resistance could be explained by an impairment in PPARγ function due to decreased production.

Thiazolidinediones (including rosiglitazone and troglitazone), synthetic ligands for PPARγ, are extensively used as a treatment for type 2 (non-insulin dependent) diabetes (Mudaliar et al., Annu. Rev. Med. 52: 239-257, 2001). Other compounds that selectively bind to the PPARγ binding domain, such as GW1929, have also been proven to be potent insulin sensitizers in vivo (Brown et al., Diabetes, 48:1415-1424, 1999). Thus, any of these compounds can be used to treat cystic fibrosis or any other disorder caused by a mutation in the CFTR gene.

Example 1

PPARγ Expression is Decreased in CFTR$^{-/-}$ Mice

An established breeding colony of exon 10 CFTR (cftr$^{-/-}$) knockout mice and wild-type littermates was used for this study. Tail-clip samples of 14-day-old male mice were processed for genotype analysis. All mice were weaned at 23 days of age and then placed on Peptamen (Nestle Clinical Nutrition, Deerfield, Ill.) and water until 30 days of age, and then continued for 10 days with 15 mL/day of Peptamen. Mice were euthanized by $CO_2$ and the organs harvested. Ileum and colon mucosal samples were prepared by opening up the intestine, removing the lumenal contents by flushing with PBS, and then scraping the mucosa from the muscle layers with a razor blade. Tissues were snap frozen in RNAlater (Ambion, Austin, Tex.) for RNA extraction (Barerett et al., Nat. Genetics 23: 32-33, 1999). For western blotting nuclear and cytoplasmic extracts were prepared as described below, and for immunohistochemistry tissues were fixed in 10% formalin.

Total RNA from cftr$^{-/-}$ and wild-type tissues was prepared using the RNA STAT-60 isolation reagent (Tel-Test, Friendswood, Tex.) and quantified spectrophotometrically. Quantitative PCR was performed in a ABI Prism 7700 Sequence Detector (Applied Biosystems, Foster City, Calif.) using the RT-PCR master mix kit (Applied Biosystems) according to the manufacturer's instructions. PCR primers, PPARγ and CFTR FAM-labeled TaqMan probes were provided by Integrated DNA Technologies (Coralville, Iowa). The oligonucleotide sequences used were the following: PPARγ exon 2 FW: 5'-tca caa gag ctg acc caa tgg t-3' (SEQ ID NO: 1), PPARγ exon 2 RV: 5'-ata ata agg tgg aga tgc agg ttc tac-3' (SEQ ID NO: 2), PPARγ probe: 5'-FAM-ctg aag ctc caa gaa tac caa agt gcg atc-TAMRA-3' (SEQ ID NO: 3), CFTR exon 2 FW: 5'-aag aat ccc cag ctt atc cac g-3' (SEQ ID NO: 4), CFTR exon 3 RV: 5'-tgg aca gcc ttg gtg act tcc-3' (SEQ ID NO: 5), and CFTR probe: 5'-FAM-cct tcg gcg atg ctt tmt ctg gag att-TAMRA-3', (SEQ ID NO: 6).

The mRNA levels were normalized by 18s ribosomal RNA expression (ribosomal RNA control reagents, Applied Biosystems) and quantified simultaneously to PPARγ or CFTR in a multiplex RT-PCR reaction. All samples were analyzed in duplicates.

RNA extracts from wild type and cftr$^{-/-}$ mice were subjected to quantitative analysis of total PPARγ. The results are shown in FIG. 1. PPARγ expression in colonic mucosa, ileal mucosa, and lung homogenate from cftr$^{-/-}$ mice were 2-fold lower as compared to wild type mice ($p<0.05$, n=5). No significant differences in mRNA expression were found either in perigonadal adipose tissue or in liver homogenate.

Accordingly, administration of a PPAR ligand (agonist) or inducer that acts in a CFTR-independent manner mitigates the symptoms associated with CFTR dysfunction.

Figure 2:
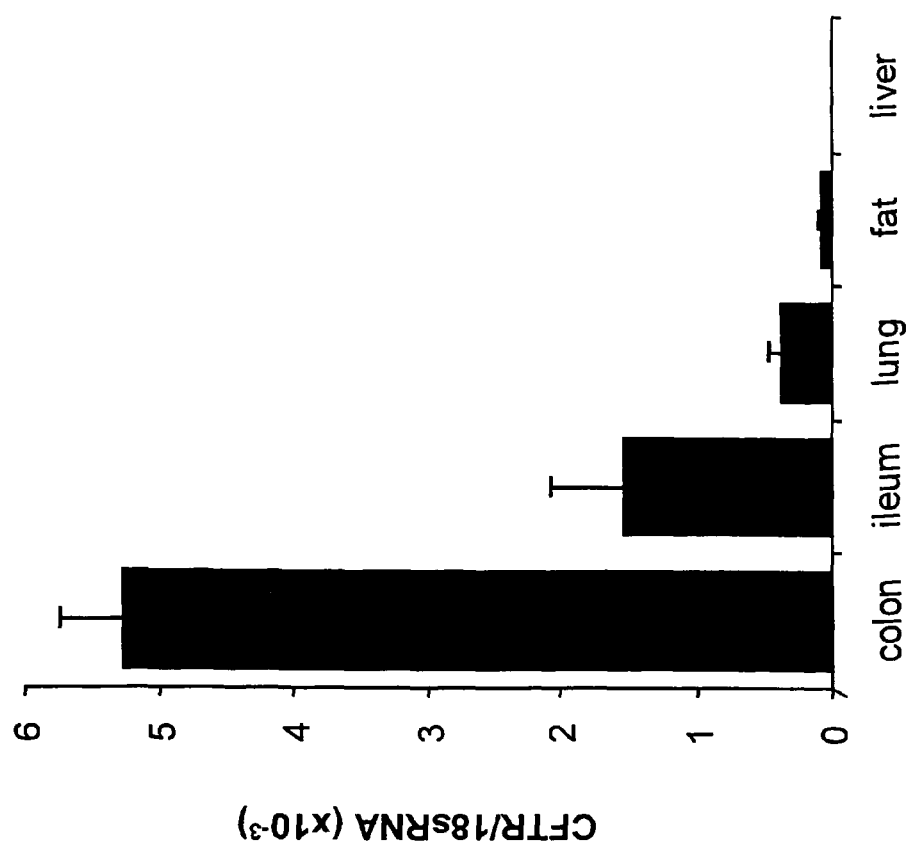
FIG. 2 is a bar graph illustrating CFTR expression in various tissues of the wild-type mice used in FIG. 1. CFTR is significantly expressed in mouse tissues showing decreased PPARγ expression. mRNA expression of CFTR was analyzed in colon, ileum, lung, fat, and liver from wild-type mice. RNA extracts were subjected to quantitative RT-PCR. Values are represented as the ratio between the respective mRNA and 18s ribosomal RNA levels. Data are expressed as means±SEM (n=4).

To evaluate a potential association between PPARγ levels and tissue-specific regulation by CFTR, CFTR RNA was quantified in parallel in these tissues from wild-type mice. The results shown in FIG. 2 demonstrate that CFTR is mostly expressed in intestinal mucosa, preferentially in colon, and at a lower extent in total lung. mRNA expression of CFTR in adipose tissue and liver was very low and in the latter, near background levels.

Example 2

Immunohistochemical Localization of PPARγ in CFTR$^{-/-}$ Mice

PPARγ immunostaining was performed using a rabbit polyclonal antibody (Cell Signaling, Beverly, Mass.). After pretreatment with 0.3% hydrogen peroxide in absolute methanol, sections were blocked with 1% BSA for 2 hours at room temperature and then incubated with the primary antibody (1:100 dilution) overnight at 4° C. This was followed with washing and incubating with biotinylated secondary antibody (1:200 dilution). Peroxidase activity was visualized with 3,3'-diaminobenzidine (DAB kit; Vector Laboratories, Burlingame, Calif.) as a substrate. Omission of the primary antibody served as a negative control.

Figure 3:
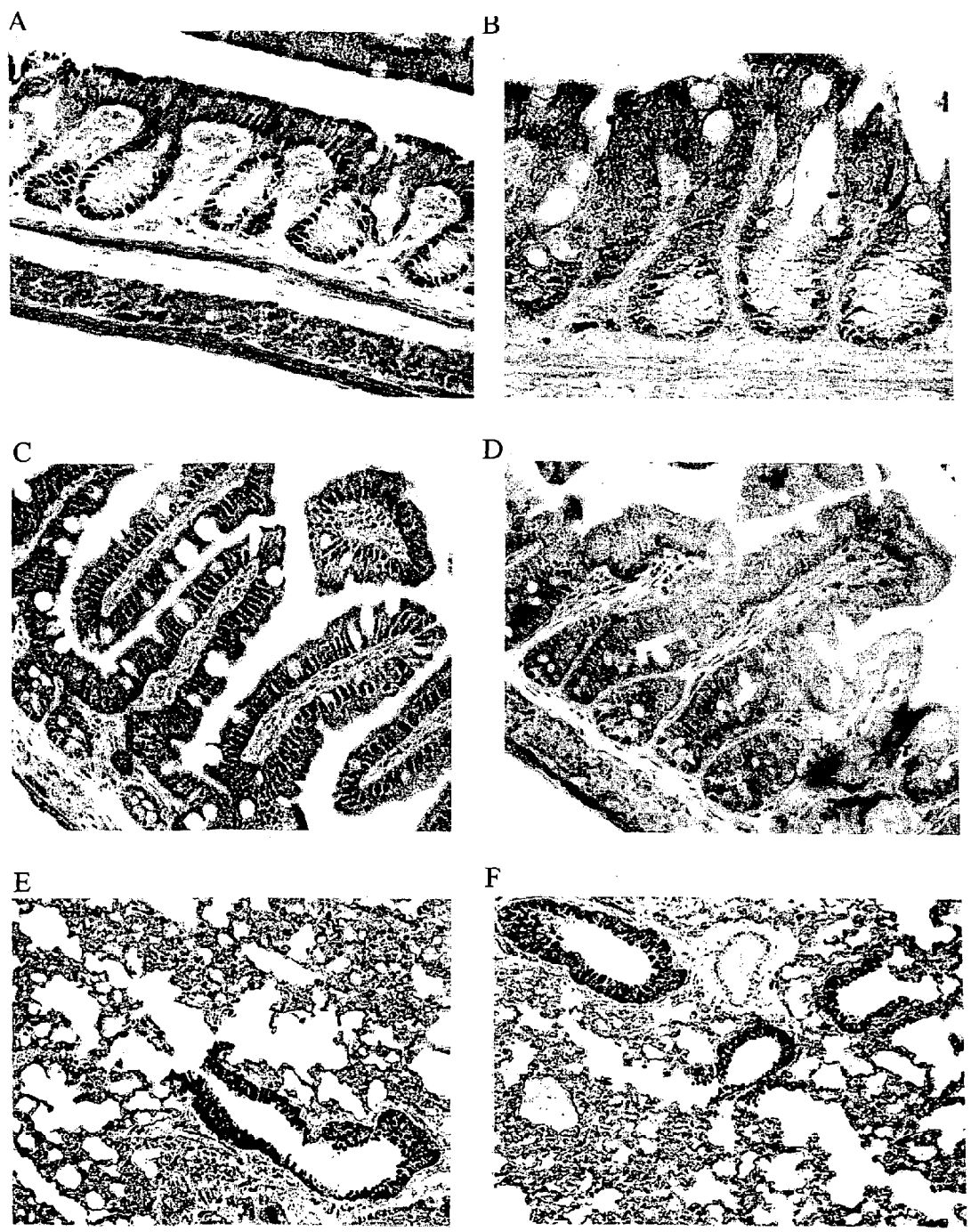
FIGS. 3A-3F are a series of photomicrographs showing the immunohistochemical distribution of PPARγ in ileum, colon and lung. PPARγ immunohistochemistry was performed on colon (FIGS. 3A and 3B), ileum (FIGS. 3C and 3D) and lung (FIGS. 3E and 3F) from wild-type (FIGS. 3A, 3C, and 3E) and cftr$^{-/-}$ (FIGS. 3B, 3D, and 3F) mice. Tissue sections were stained with a rabbit polyclonal anti-PPARγ antibody and a biotinylated secondary antibody. Sections from cftr$^{-/-}$ and wild-type mice correspond to equivalent tissue regions. Magnification is 200× for FIGS. 3A-D and 100× for FIGS. 3E and 3F. Incubation in the absence of primary antibody showed no staining.

PPARγ was predominantly localized to nuclei in the mucosal layer of colon and ileum in wild-type mice, (FIGS. 3A and 3C). In contrast, the colon and ileum mucosa from cftr$^{-/-}$ mice showed reduced nuclear labeling and a predominant diffuse cytoplasmic staining (FIGS. 3B and 3D). Analysis of lung tissue showed a mixed labeling of both nuclei and cytoplasm localized to larger bronchi and a diffuse lighter staining of the remaining tissue (FIGS. 3E and 3F) in both wild-type and cftr$^{-/-}$ mice.

Example 3

Reduced PPARγ Levels in Colonic Epithelium Nuclei of CFTR$^{-/-}$ Mice

For western blotting of total, nuclear, and cytosolic extracts, tissue samples were harvested, minced, and homogenized in 0.5 ml of hypotonic buffer (20 mM Hepes pH 7.5, 5 mM NaF, 0.1 mM EDTA, 1 mM Na$_3$VO$_4$) containing 0.01% NP-40 with a pre-chilled Dounce homogenizer. The suspension was incubated 15 minutes on ice followed by centrifugation for 10 min at 850×g at 4° C. The supernatants (cytoplasmic fraction) were transferred and the pellets were resuspended in 0.5 ml hypotonic buffer containing 0.5% of NP-40, incubated 15 minutes at 4° C., centrifuged 30 sec at 14000×g and the supernatants discarded. Pellets, representing the nuclear fraction, were resuspended in 50 μl of lysis buffer (20 mM Hepes pH 7.5, 400 mM NaCl, 20% Glycerol, 0.1% EDTA, 10 mM NaF, 10 μM Na$_2$MO$_4$, 1 mM NaVO$_3$, 10 mM PNPP, 10 mM β-glycerophosphate) containing 1 mM DTT and Complete Mini EDTA-free protease inhibitor cocktail (Roche Diagnostics, Indianapolis, Ind.). Protein concentration in all samples was measured by Bradford protein assay (Bio-Rad, Hercules, Calif.). Equal amounts of proteins were subjected to SDS-10% PAGE, electrotransferred onto immobilon-P (Millipore, Billerica, Mass.), then immunoblotted for PPARγ (1:2000 dilution). Densitometric analysis was performed using by National Institutes of Health Image 1.62 program.

Figure 4:
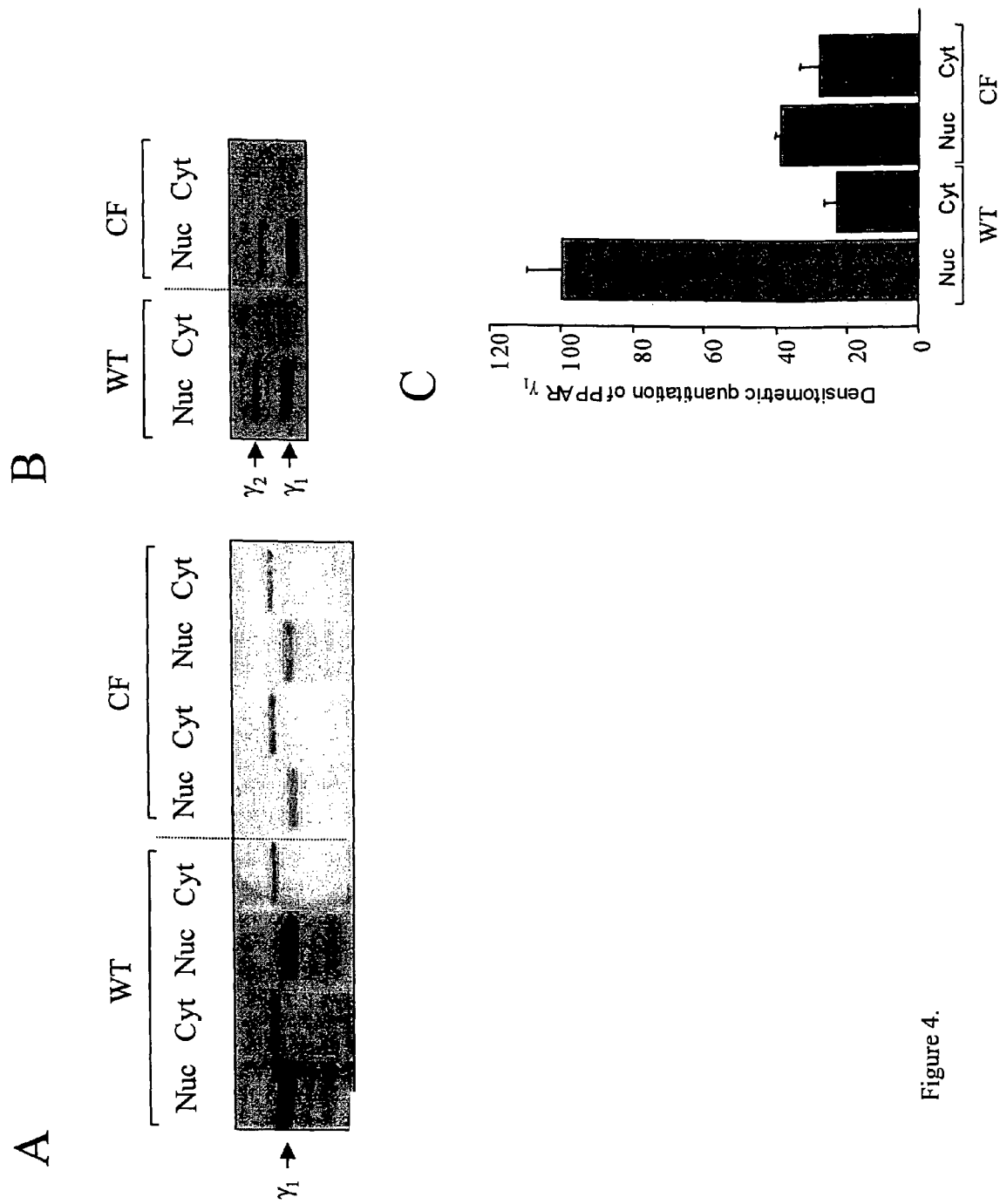
FIGS. 4A and 4B are western blots of PPARγ protein expression in the nuclear and cytosolic compartments of colon and fat cells. Western blot analysis of PPARγ was performed on nuclear (Nuc) and cytosolic (Cyt) extracts from colon (FIG. 4A) and perigonadal fat (FIG. 4B) from wild type (WT) and cftr$^{-/-}$ (CF) mice. Protein extracts were subjected to western blotting using a rabbit polyclonal anti-PPARγ antibody. Samples from two wild-type and two cftr$^{-/-}$ mice are shown from the colon.
FIG. 4C is a bar graph showing the densitometric quantification for colonic samples from 3 wild-type and 3 cftr$^{-/-}$ mice. Background was subtracted from bands. Values are expressed as the mean±SEM relative to WT, where 100% is the mean value.

Western blotting was performed in order to confirm the findings revealed by immunohistochemistry of a redistribution of PPARγ from predominantly nuclear to a less intense but more equal partitioning between nuclear and cytoplasmic compartments in ileum and colon. As shown in FIG. 4A, levels of PPARγ in colon from wild-type mice were significantly higher in the nuclear compared to the cytosolic fractions with the band in the cytoplasmic fraction exhibiting a slower mobility on SDS-PAGE. In contrast, PPARγ levels in cftr$^{-/-}$ mice were decreased with similar amounts observed between the nuclear and cytosolic fractions. This is shown quantitatively in FIG. 4C where the principal difference in cftr$^{-/-}$ mice compared to wild-type controls is a decrease in the nuclear fraction with little change in cytosolic quantities.

Perigonadal fat was also examined. As shown in FIG. 4B, both isoforms of PPAR are seen in adipocytes with PPARγ2 having a higher apparent molecular weight compared to PPARγ1. No differences were seen in PPARγ levels in fat comparing cftr$^{-/-}$ mice with wild-type littermates.

PPARγ is known to migrate as two different bands by SDS-PAGE and has been attributed to post-translational modification. The higher apparent molecular weight form is due to phosphorylation following insulin stimulation in NIH 3T3 cells or in human colorectal HCT-116 cells. In addition, nitration of tyrosine residues on PPARγ has been demonstrated in macrophage-like RAW 264 cells in response to TNF or lipopolysaccharide resulting in inhibition of ligand-dependent translocation to the nucleus. These postranslational modifications likely explain the two forms of PPARγ seen on our western blots (FIGS. 4A and 4B). The higher apparent molecular weight form (around 3 kDa) seen in the cytosolic fractions is not PPARγ2 based on comparison with results obtained with adipose tissue.

Example 4

Figure 5:
FIGS. 5A-5D are a series of photomicrographs showing the immunohistochemical distribution of PPARγ in intestinal epithelium of cftr$^{-/-}$ mice after rosiglitazone treatment. Wild-type and cftr$^{-/-}$ mice were given rosiglitazone by gavage for 9 days. Colon (FIGS. 5A and 5B) and ileum (FIGS. 5C and 5D) were analyzed from wild-type (FIGS. 5A and 5C) and cftr$^{-/-}$ (FIGS. 5B and 5D) mice. Magnification is 200×.
Figure 5:
Figure 5:
Figure 5:
Figure 6:
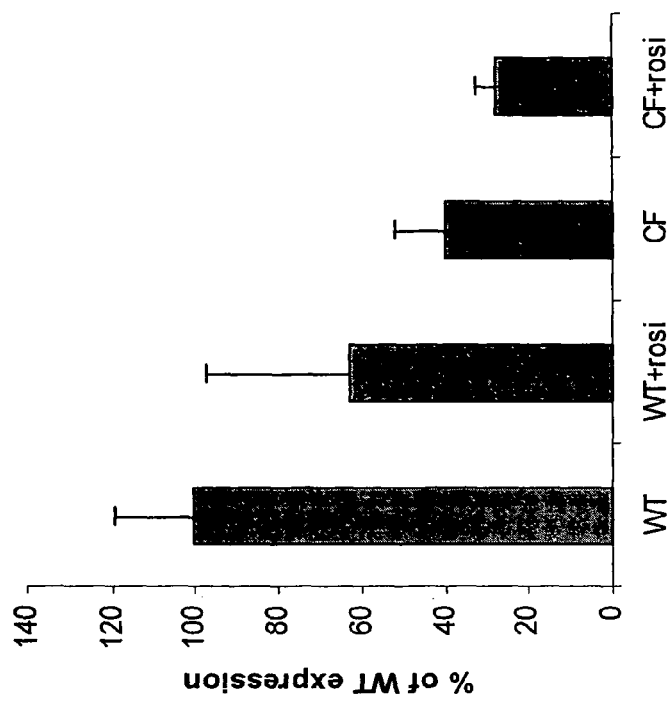
FIGS. 6A-6B are bar graphs showing the PPARγ mRNA expression in the colon (FIG. 6A) and ileum (FIG. 6B) following rosiglitazone treatment of wild-type (WT) and cftr$^{-/-}$ (CF) mice. RNA extracts were subjected to quantitative RT-PCR. Values are expressed relative to WT, where 100% is the mean value in each of the respective tissues. Data are expressed as means±SEM (n=5).
Figure 6:
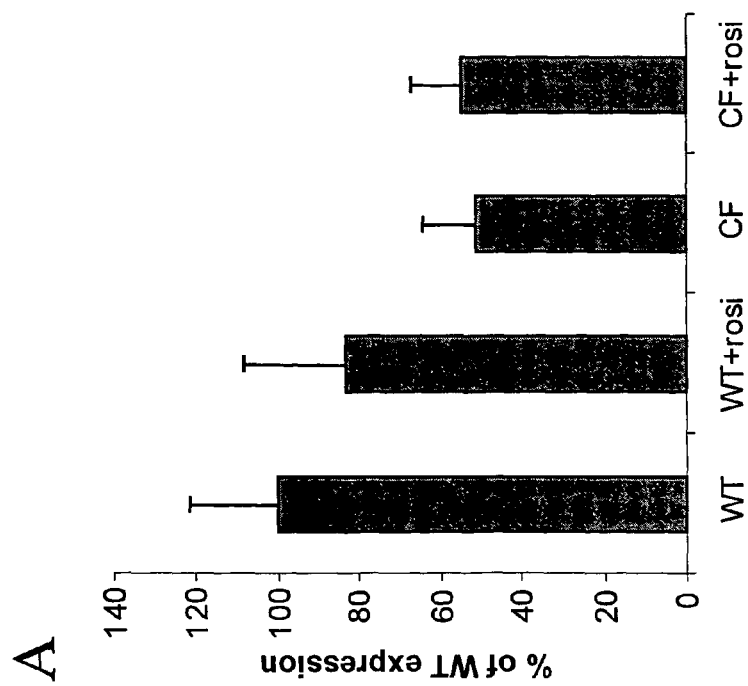

Rosiglitazone Increases Nuclear Localization of PPARγ Without Affecting RNA Expression In order to determine whether rosiglitazone, a synthetic PPARγ ligand, increases nuclear localization and/or increases RNA expression, 3 mg/kg of rosiglitazone (GlaxoSmithKline, Philadelphia, Pa.) was administered by gavage once a day for 9 days. Immunohistochemical analysis of PPARγ showed very strong nuclear labeling in both colon and ileum from wild-type mice (FIGS. 5A and C, respectively). In contrast to the decreased nuclear staining of both tissues in cftr$^{-/-}$ mice (FIGS. 3B and 3D), treatment with rosiglitazone led to a dramatic increase in nuclear labeling (FIGS. 5B and 5D). As shown in FIGS. 6A and 6B, rosiglitazone did not increase RNA expression in either the colonic (FIG. 6A) or the ileal (FIG. 6B) mucosa, compared to controls.

Example 5

PPARγ DNA Binding is Altered in the Colonic Musoca of CFTR$^{-/-}$ Mice

Electrophoretic mobility shift assays (EMSA) were performed as described Tzameli et al. (Mol. Cell. Biol. 20: 2951-2958, 2000). Briefly, double-stranded oligonucleotides containing either a perfect DR1 motif (synthetic PPARγrecognition element (PPRE): 5' agc tac gtg acc ttt gac ctg gt-3' (SEQ ID NO:7)) or the PPRE from the mouse acyl-CoA oxidase promoter (5'-aca ggg gac cag gac aaa ggt cac gtt cgg gag t-3' (SEQ ID NO:8)) were end-labeled with [γ-32P] ATP (PerkinElmer, Boston, Mass.) and incubated with 10 mg of nuclear extracts, for 20 minutes at room temperature. To test specificity, a rabbit polyclonal PPARγ specific antibody against the C-terminal part of the protein (Santa Cruz Biotechnology, Santa Cruz, Calif.) was incubated with the nuclear extracts for 30 minutes, prior to the addition of the probe. Competition for specific binding was performed by adding excess of unlabeled oligonucleotide to the reaction, also 30 minutes prior to the addition of the probe. The complexes were resolved on a 4% nondenaturing polyacrylamide gel and visualized by autoradiography.

Figure 7:
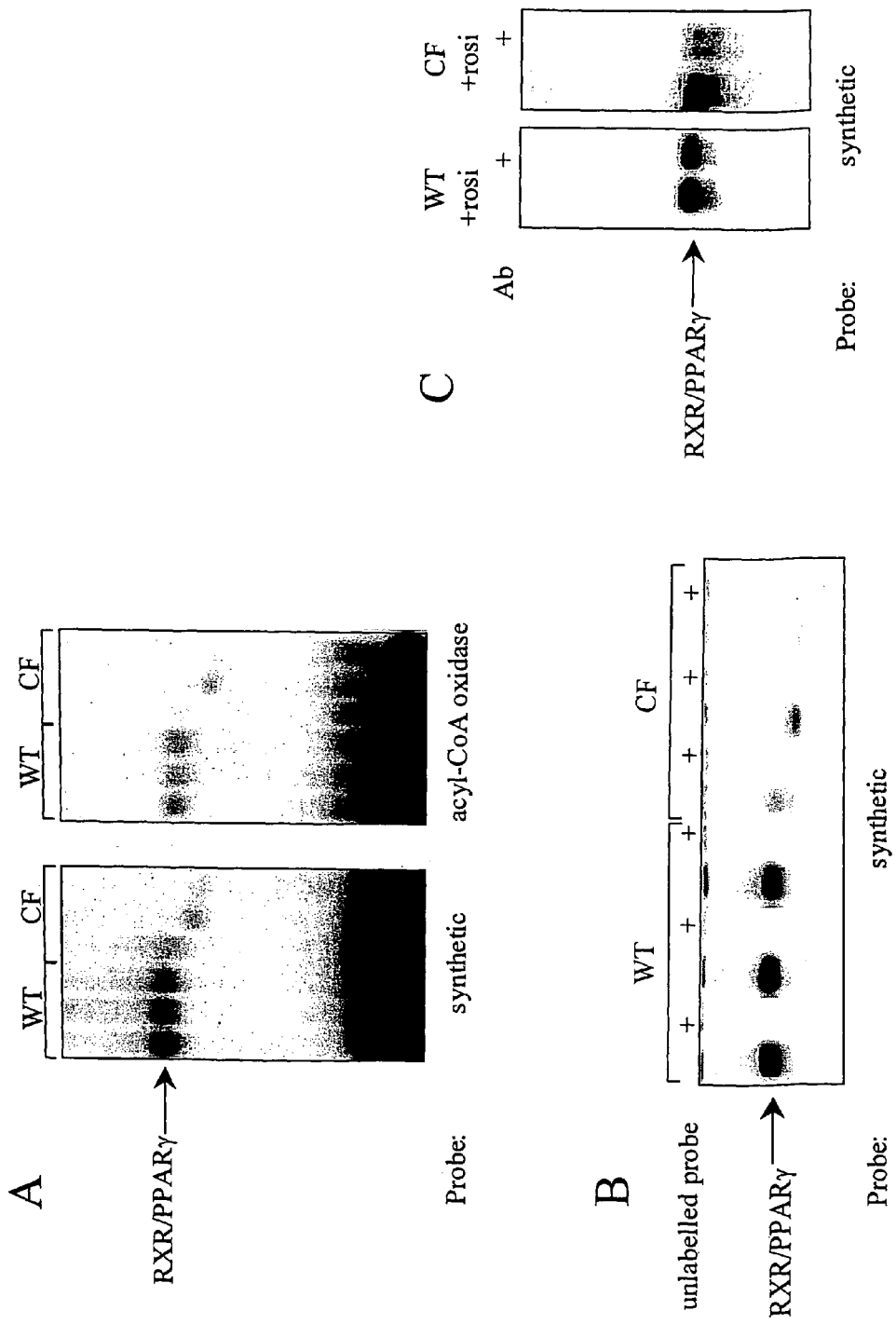
FIGS. 7A-7B are a series of electrophoretic gels showing the differential PPARγ binding to PPRE in mouse colonic mucosa. PPARγ DNA binding was analyzed by EMSA in colonic mucosa of wild type (WT) and cftr$^{-/-}$ (CF) mice. Colon nuclear extracts were used as a source of protein. Oligonucleotide probes carrying a perfect DR1 motif of the PPRE from the acyl-CoA oxidase promoter were used as probes. Each lane contains protein sample from a different mouse and 3 different samples from each genotype were used.
FIG. 7C is a supershift assay of samples from WT and CF mice treated with rosiglitazone. A rabbit polyclonal anti-PPARγ antibody against the C-terminus was used.

The decrease in nuclear PPARγ protein expression in colon from cftr$^{-/-}$ mice demonstrated by western blotting, suggests that an equal decrease in PPARγ DNA binding activity to its consensus site should be observed. EMSA analysis of nuclear proteins from wild-type and cftr$^{-/-}$ mice was performed using both synthetic PPRE and the natural PPRE from the acyl-CoA oxidase promoter, both oligonucleotides used, in the cftr$^{-/-}$ mice (FIG. 7A). Reduced binding of the PPARγ/RXR heterodimer from nuclear extracts of cftr$^{-/-}$ mice was seen compared to wild-type controls. In addition, a faster migrating complex was apparent in 2 of the 3 cftr$^{-/-}$ mouse protein samples. In order to test for specificity of this shift, competition analysis was performed. As shown in FIG. 7B, a 100-fold excess of unlabeled oligonuleotide efficiently competed for binding of the wild-type and the cftr$^{-/-}$ mouse samples to the synthetic PPRE. This suggests that binding is specific and that the faster migrating complex seen in cftr$^{-/-}$ samples may represent a proteolytic fragment of the proteins containing an intact DNA binding domain. Protein extracts from perigonadal fat of both wild-type and cftr$^{-/-}$ mice, which contain minimal amounts of CFTR, demonstrated equally strong binding of the PPARγ/RXR heterodimer to the synthetic PPRE.

Example 6

Rosiglitazone Treatment Corrects the PPARγ Binding Defect in CFTR$^{-/-}$ Mice

In agreement with the immunohistochemical analysis of wild-type and cftr$^{-/-}$ mice, rosiglitazone treatment also led to a significant increase in the binding of the PPARγ/RXR heterodimer to the synthetic PPRE (FIG. 7C). Colon protein samples from both genotypes produced a strong band on the gel. Specificity of this shift was tested by incubation with a rabbit polyclonal antibody against the C-terminal part of PPARγ. Addition of antibody reduced the binding in both samples tested. Again, no differences in the binding of the PPARγ/RXR heterodimer to the synthetic PPRE between perigonadal fat protein extracts of rosiglitazone treated wild-type and cftr$^{-/-}$ mice were observed.

Example 7

Decreased PPARα is Associated with Bile Duct Injury in cftr$^{-/-}$ Mice

Primary sclerosing cholangitis (PSC) is a chronic liver disease characterized by fibro-obliterative inflammation of the biliary tract. Although the etiology and pathogenesis of PSC is not known, it is strongly associated with ulcerative colitis and Crohn's disease in approximately 80% of cases (Broome et al., Gut, 4:610-615, 1996; Farrant et al., Gastroenterology, 100:1710-1717, 1991). Conversely, 2.5-7.5% of patients with inflammatory bowel disease develop PSC (Lee et al., N. Engl. J. Med., 332:924-933, 1995) although the mechanism by which these patients are predisposed to bile duct inflammation is unknown.

Cholestasis, chronic inflammation, and portal tract damage characterize both PSC and cystic fibrosis liver disease, with cholangiographic findings of stricturing and beading observed in both diseases (Nagel et al., Lancet, 2:1422-1425, 1989; O'Brien et al., Gut, 33:387-391, 1992). CFTR expression in the hepatobiliary system is localized to the apical membrane of the intrahepatic and extrahepatic bile duct epithelial cells where it plays a major role in biliary fluid secretion (Cohn et al. Gastroenterology, 105:1857-1864, 1993). Hence, mutations in the CFTR gene result in the formation of inspissated biliary secretions. In addition, CFTR dysfunction results in an excessive host inflammatory response (Khan et al., Am. J. Respir. Crit. Care Med., 151:1075-1082, 1995; Muhlebach et al., Am. J. Respir. Crit. Care Med., 160:186-191, 1999).

Due to the similarities between PSC and the liver disease in CF, studies have examined the prevalence of CFTR mutations in adults with PSC. In one study, only 1 of 19 subjects with PSC had neither a CFTR mutation/variant nor the M470V genotype (Sheth et al., Human Genetics, 113:286-292, 2003). CFTR function in these patients was decreased as measured by nasal transmembrane potential difference testing. Another study failed to demonstrate an association of common CF disease-causing mutations with PSC (Gallegos-Orozco et al., Am. J. Gastroenterol., 100: 874-878, 2005). However, exhaustive genotyping as well as functional analyses were not performed in that study. Further support for the concept that CFTR dysfunction in the setting of colitis predisposes to bile duct injury comes from experiments with exon 10 cftr$^{-/-}$ mice where induction of colitis with dextran sodium sulfate (DSS) results in a mononuclear cell infiltrate in the portal tracts in conjunction with bile duct proliferation (Blanco et al., Am. J. Physiol. Liver Physiol., 287:G491-G496, 2004). This was not observed in wild-type (WT) controls.

In order to understand the mechanism by which CFTR dysfunction leads to the phenotypic expression of CF, multiple studies in both humans and mice have demonstrated a link to abnormalities in fatty acid metabolism. Arachidonic Acid (AA) is increased and Docosahexaenoic Acid (DHA) decreased in lung, pancreas, and ileum from cftr$^{-/-}$ mice (Freedman et al., Proc. Nat'l. Acad. Sci. U.S.A., 96:13995-14000, 1999) as well as in tissue and plasma from humans with CF (Freedman et al., N. Engl. J. Med., 350:560-569, 2004). In cftr$^{-/-}$ mice, oral DHA corrected this fatty acid defect and reversed the pathology in CF affected organs. Similarly, oral administration of DHA was found to prevent the development of bile duct injury in cftr$^{-/-}$ mice in response to DSS induced colitis based on histology and serum alkaline phosphatase levels (Blanco, P. G. et al., supra).

Abnormalities in PPAR function would link the enhanced innate immune response and the alterations in fatty acid metabolism seen in CF. In the study described below, we hypothesized that 1) CFTR dysfunction by reducing PPARα and/or γ expression in the liver leads to bile duct injury in cftr$^{-/-}$ mice, and 2) DHA prevents bile duct injury through an increase in PPARα or γ expression in the liver. To evaluate this, we examined whether PPARα or γ expression is decreased in the liver of cftr$^{-/-}$ mice compared to WT littermates following DSS and whether the protective mechanism of action of DHA is through modulation of PPARα or γ. The role of PPARα alone in the genesis of bile duct injury was tested by histologic examination of the liver from PPARα$^{-/-}$ mice treated with DSS.

Materials and Methods

Breeding of Mice

The Beth Israel Deaconess Medical Center Institutional Animal Care and Use Committee approved all protocols. University of North Carolina heterozygous CFTR exon 10 C57/BL6 transgenic knockout mice (Jackson Laboratory, Bar Harbor, Me.) were bred to produce WT and null mice and utilized for all experiments. The tails of 14-day old mice were clipped and processed for analysis of genotype as previously described (Zeng, W. et al., Am. J. Physiol. Cell Physiol., 273:C442-C445 (1997)). Cftr$^{-/-}$ and WT mice were weaned at 23 days and placed on water and Peptamen (Nestle Clinical Nutrition, Deerfield, Ill.). PPARα$^{-/-}$ mice with an Sv/129 genetic background and Sv/129 WT mice as strain controls were also obtained from Jackson Laboratories.

Dextran Sodium Sulfate Induced Bile Duct Injury

On day 40, WT and cftr$^{-/-}$ mice were fed Peptamen alone or Peptamen plus 125 mg DSS/day (MP Biomedicals, Aurora, Ohio) for 5 days followed by 9 days of 85 mg DSS/day as previously described for the genesis of bile duct injury (Blanco, P. G. et al., supra). The amount of DSS in Peptamen was equally measured for WT and cftr$^{-/-}$ mice. The volume of Peptamen administered (20 ml) was measured on a daily basis. There was no difference in Peptamen intake between WT and cftr$^{-/-}$ mice. The mean weight of WT mice at the start of DSS treatment was 20.5 g (range 14.5-26 g), and the mean weight of cftr$^{-/-}$ mice was 18.9 g (range 15.5-23.5 g). These values were not statistically different between WT and cftr$^{-/-}$ mice. The degree of colitis was similar between WT and cftr$^{-/-}$ mice as determined by visualization of bloody diarrhea in all animals and histological evidence demonstrating features of colitis with mononuclear cell infiltrates, loss of crypts, and mucosal ulcerations in the colonic resection specimens. There was no difference in weight lost during DSS treatment comparing WT and cftr$^{-/-}$ mice. Additional mice from these groups were given DHA (Pure Encapsulations, Sudbury, Mass.) prepared as a stable emulsion in Peptamen, at a dose of 40 mg per day for 5 days before and continued for 14 days during administration of the DSS. Bile duct injury was quantified, as previously described, by examining histological features of epithelial injury, bile duct proliferation, and bile duct angulation (Blanco et al., supra). To determine whether a complete absence of PPARα was responsible for the bile duct injury, 5 PPARα$^{-/-}$ mice were treated with 5% DSS in drinking water for 7 days to induce colitis (Okayasu et al., Gastroenterology, 98:694-702, 1990). PPARγ$^{-/-}$ mice are not viable and thus were not tested.

Analysis of PPAR Expression

After each specific treatment, the mice were euthanized with carbon dioxide. Tissues were snap frozen in RNAlater (Ambion, Austin, Tex.) for RNA extraction (Barrett et al., Nat Genet, 23:32-33, 1999). PPAR mRNA analyses were performed by quantitative RT-PCR. Total RNA from cftr$^{-/-}$ and WT tissues was prepared using the RNA STAT-60 isolation reagent (Tel-Test, Friendswood, Tex.) and quantified spectrophotometrically. Quantitative PCR was performed in an ABI Prism 7700 Sequence Detector (Applied Biosystems, Foster City, Calif.) using a RT-PCR master mix kit (Applied Biosystems) according to the manufacturer's instructions. PCR primers and PPAR FAM-labeled TaqMan probes were from Integrated DNA Technologies (Coralville, Iowa). The oligonucleotide sequences used for PPARγ were the following: PPARγ exon 2 FW 5'-TCA CAA GAG CTG ACC CAA TGG T-3' (SEQ ID NO: 1), PPARγ exon 2 RV 5'-ATA ATA AGG TGG AGA TGC AGG TTC TAC-3' (SEQ ID NO: 2), PPARγ probe 5'-FAM-CTG AAG CTC CAA GAA TAC CAA AGT GCG ATC-TAMRA-3' (SEQ ID NO: 3). The sequences used for PPARα were the following: PPARα FW 5'-TAT TCG GCT GAA GCT GGT GTA C-3' (SEQ ID NO: 9), PPARα RV 5'-CTG GCA TTT GTT CCG GTT CT-3' (SEQ ID NO: 10), PPARα probe 5'-CTG AAT CTT GCA GCT CCG ATC ACA CTT G-3' (SEQ ID NO: 11). Levels of mRNA were normalized to 18s ribosomal RNA (ribosomal RNA control reagents, Applied Biosystems) quantified simultaneously to PPAR in a multiplex RT-PCR reaction. Thermocycler conditions used were—Stage 1: 48° C./30 minutes; Stage 2: 95° C./10 minutes; Stage 3: 40 cycles of 95° C./15 seconds and 60° C./60 seconds. All samples were analyzed in duplicate.

For immunohistochemistry, tissue samples were fixed in 10% formalin. Samples were embedded in paraffin, 5 μm sections prepared, and stained with haematoxylin and eosin (H&E) for light microscopic examinations. PPARα immunostaining was performed using a rabbit polyclonal antibody (Affinity Bioreagents, Golden Colo.). After pretreatment with 0.3% hydrogen peroxide in absolute methanol, sections were blocked with 1% BSA for 2 hours at room temperature and then incubated with the primary antibody (1:100 dilution) overnight at 4° C. This was followed with washing and incubating with biotinylated secondary antibody (1:200 dilution). Peroxidase activity was visualized with 3,3-diaminobenzidine (DAB kit; Vector Laboratories, Burlingame, Calif.) as a substrate. Omission of the primary antibody served as a negative control.

For western blotting, nuclear and cytoplasmic extracts were prepared as described previously (Ollero et al., supra). Briefly, tissue samples were harvested, minced, and homogenized with a pre-chilled Dounce homogenizer in 0.5 ml of hypotonic buffer (20 mM Hepes pH 7.5, 5 mM NaF, 0.1 mM EDTA, 1 mM Na$_3$VO$_4$, 10 μM Na$_2$MoO$_4$) containing 0.01% NP-40, 1 mM DTT and protease inhibitor. The suspension was incubated 15 minutes on ice followed by centrifugation for 10 minutes at 850×g at 4° C. The supernatants (cytoplasmic fraction) were transferred and the pellets were resuspended in 0.5 ml hypotonic buffer containing 0.5% of NP-40, incubated 15 minutes at 4° C., centrifuged 30 seconds at 14000×g and the supernatants discarded. Pellets, representing the nuclear fraction, were resuspended in 50 μl of lysis buffer (20 mM Hepes pH 7.5, 400 mM NaCl, 20% Glycerol, 0.1% EDTA, 10 mM NaF, 10 μM Na$_2$MoO$_4$, 1 mM NaVO$_3$, 10 mM PNPP, 10 mM β-glycerophosphate) containing 1 mM DTT and Complete Mini EDTA-free protease inhibitor cocktail (Roche Diagnostics, Indianapolis, Ind.). Protein concentration was measured in all samples by the Bradford protein assay (Bio-Rad, Hercules, Calif.). Equal amounts of proteins were subjected to SDS-10% PAGE, electrotransferred onto immobilon-P (Millipore, Billerica, Mass.), then immunoblotted for PPARα (1:2,000 dilution of rabbit polyclonal primary antibody (Affinity Bioreagents, Golden, Colo.) followed by 1:4,000 of goat anti-rabbit HRP antibody). Chemiluminescence detection was performed using lumiGLO reagent (Cell Signaling). Densitometric analysis was performed using the National Institutes of Health Image 1.62 program.

Analysis of TNFα Levels

The liver tissue was homogenized with 500 μl of RIPA buffer (150 mM NaCl, 1.0% Triton X-100, 0.1% SDS, 10 mM Tris-HCl and 1 mM EDTA, pH 7.4 with protease inhibitor cocktail). The homogenate was centrifuged at 15,000 rpm for 15 minutes to collect supernatants. The amounts of TNFα in the samples were quantified using the sandwich ELISA.

Statistical Analysis

T-tests were performed to determine significance of TNFα and densitometry results. The RT-PCR and densitometry results are expressed as mean values±SE. TNFα results are expressed as mean values±SD. We used both ANOVA and Kruskal-Wallis tests to determine overall significance of individual comparison groups for RT-PCR. Due to small sample size, we used Wilcoxon Rank sum test post-hoc.

Results

Figure 8:
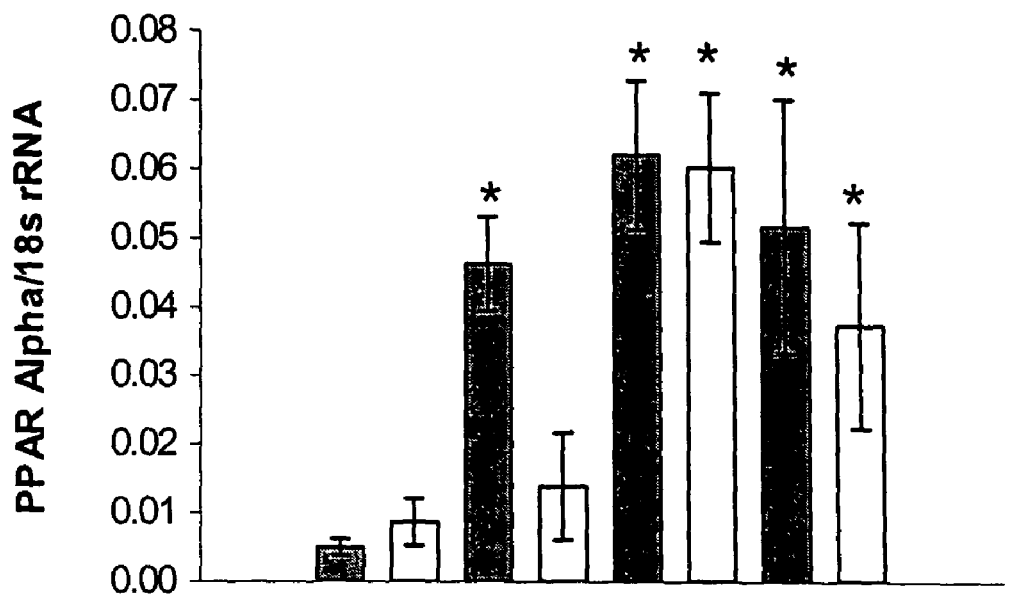
FIG. 8 is a bar graph showing expression of PPARα mRNA in response to dextran sodium sulfate (DSS) and DHA. RNA extracts were subjected to quantitative RT-PCR. The Y-axis represents mRNA levels normalized to 18s rRNA. Results are expressed as means±SE. *p<0.05. Three to five mice were used per group.

In order to determine if PPARα or γ mRNA levels are decreased in the setting of CFTR dysfunction, RNA extracts from the liver of WT and cftr$^{-/-}$ mice were subjected to quantitative RT-PCR. As shown in FIG. 8, liver PPARα levels by RT-PCR exhibited no difference between WT and cftr$^{-/-}$ control littermates. WT mice given DSS showed a 9.3 fold increase in PPARα mRNA (p=0.02). In contrast, cftr$^{-/-}$ mice exhibited no significant change in mRNA levels. The role of DHA as a potential inducer of PPAR expression was examined. In the absence of DSS, DHA treatment led to a 12.1 fold increase in liver PPARα mRNA levels in WT mice (p=0.02) and 7.0 fold increase in cftr$^{-/-}$ mice (p=0.007), compared to no DHA. The combination of both DSS and DHA led to a 10.4 fold increase in PPARα mRNA in WT mice (p=0.02) and a 4.3 fold increase in cftr$^{-/-}$ mice (p=0.04), compared to no DSS and no DHA. The combination of DSS and DHA led to a 2.7 fold increase in PPARα mRNA in cftr$^{-/-}$ mice compared to cftr$^{-/-}$ mice treated only with DSS, but this increase was not statistically significant.

Figure 9:
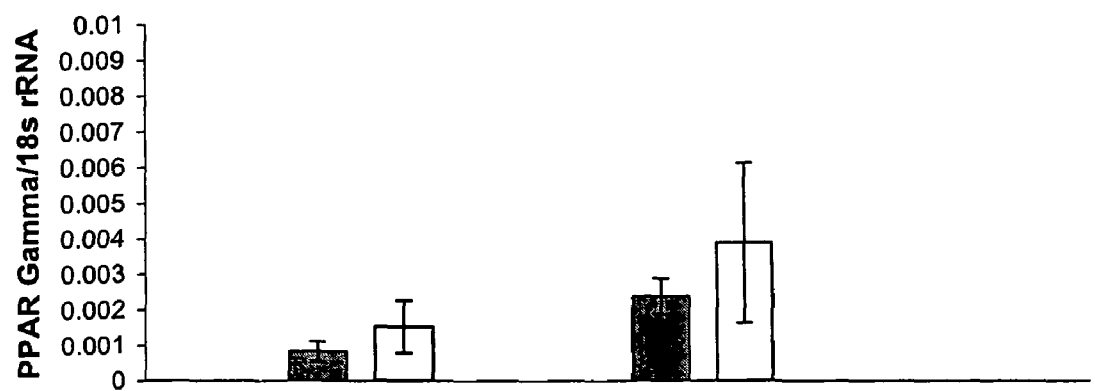
FIG. 9 is a bar graph showing expression of PPARγ mRNA in response to DSS and DHA. RNA extracts were subjected to quantitative RT-PCR. The Y-axis represents mRNA levels normalized to 18s rRNA. Results are expressed as means±SE. Three to five mice were used per group.

As shown in FIG. 9, PPARγ mRNA levels were low compared to PPARα expression and showed little difference between WT and cftr$^{-/-}$ control littermates. There was no significant change with the addition of DHA to either group of animals. With DSS treatment in the absence or presence of DHA, PPARγ mRNA levels were markedly suppressed in both WT and cftr$^{-/-}$ mice to undetectable levels. Based on the lack of differences between WT and cftr$^{-/-}$ mice and the low levels of PPARγ mRNA expression, all subsequent analyses focused on PPARα.

Figure 10:
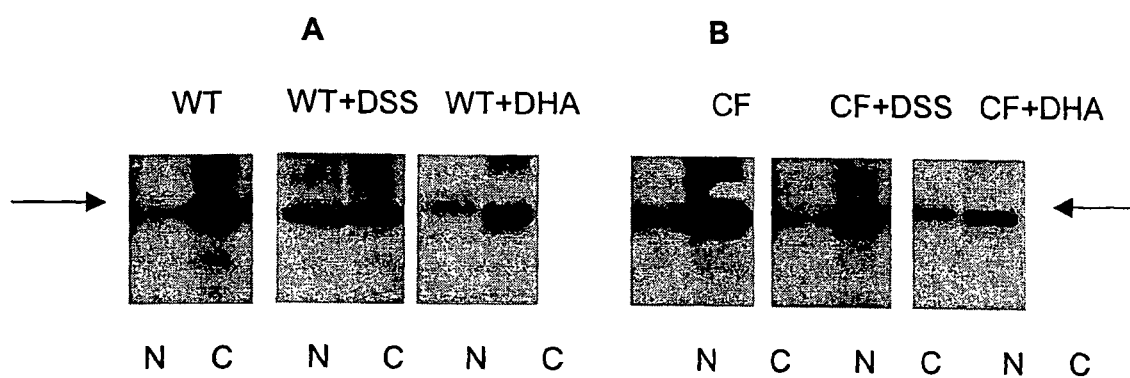
FIGS. 10A and 10B are western blots showing PPARα protein expression in nuclear and cytosolic compartments in response to DSS and DHA in wild type (FIG. 10A) and cftr$^{-/-}$ (FIG. 10B) mice. Western blot analysis of PPARα was performed on nuclear (N) and cytosolic (C) extracts from liver homogenate. The arrow indicates PPARα. Results are representative of three mice per group.

To determine if the changes in PPARα mRNA were reflected at the protein level and whether nuclear translocation was altered in cftr$^{-/-}$ mice, western blot analyses were performed. Although cftr$^{-/-}$ mice had a greater amount of PPARα protein per mg of total liver homogenate, both cftr$^{-/-}$ and WT control littermates exhibited little difference in PPARα nuclear/cytoplasmic ratio, as shown in the representative western blots in FIGS. 10A and 10B. By densitometric quantitation with 3 mice per group, the mean nuclear/cytoplasmic ratio in WT mice was 0.39±0.08, with similar results seen in cftr$^{-/-}$ mice as evidenced by a nuclear/cytoplasmic ratio 0.52±0.04 (p=0.22). The administration of DSS resulted in nuclear translocation of PPARα in WT mice (nuclear/cytoplasmic ratio 1.06±0.05, p=0.002), but not in cftr$^{-/-}$ mice treated with DSS (nuclear/cytoplasmic ratio 0.61±0.02, p=0.15). DHA did not cause translocation in either WT (0.41±0.09, p=0.90) or cftr$^{-/-}$ mice (0.54±0.06, p=0.81).

Figure 11:
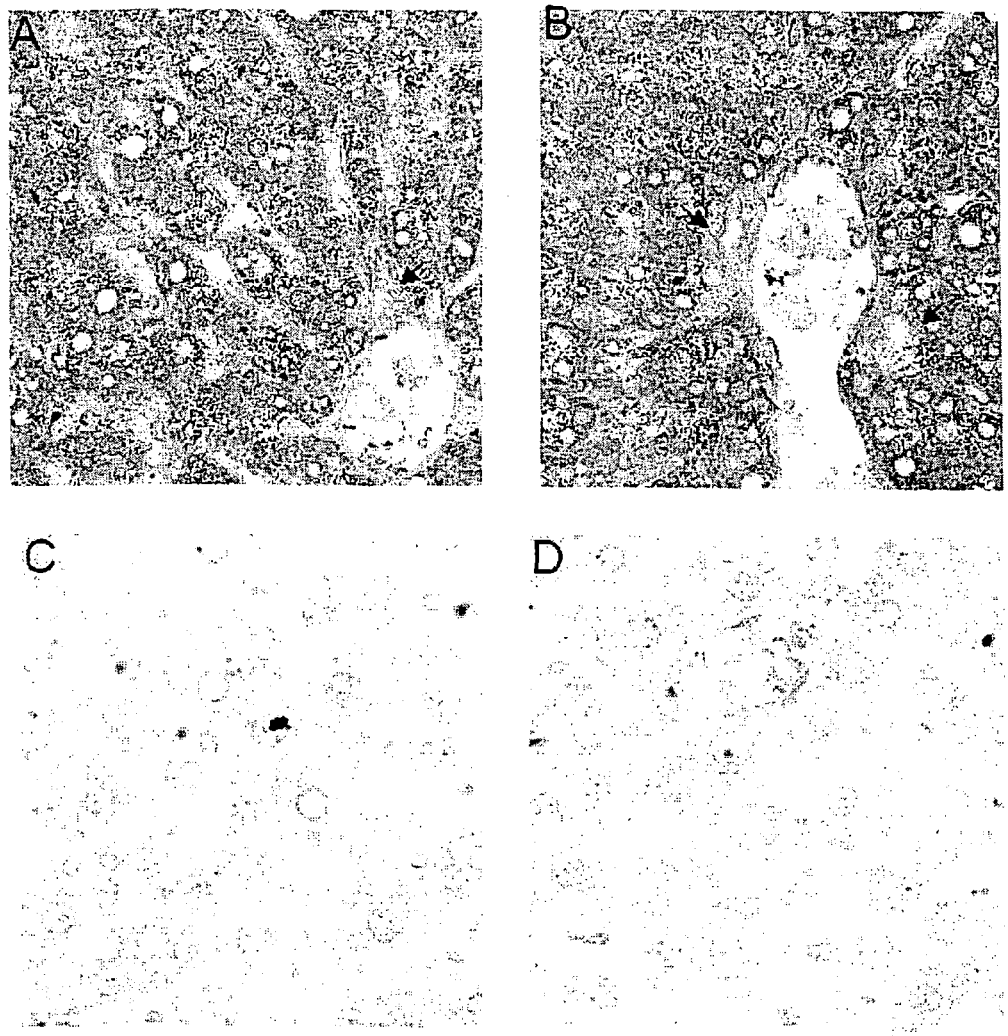
FIGS. 11A-11D are a series of photomicrographs showing the distribution of PPARα in the liver by immunohistochemistry. Liver tissue sections from WT mice (FIG. 11A) and from cftr$^{-/-}$ (FIG. 11B) were stained with a rabbit polyclonal anti-PPARα antibody and a biotinylated secondary antibody. The black arrows point to normal appearing bile ducts. Incubation in the absence of primary antibody showed no staining (bottom panels) in WT (FIG. 11C) and cftr-1 mice (FIG. 11D). Magnification is 400×.

To determine if differences in PPARα localization may explain the previous observations, immunohistochemical studies were performed. Immunohistochemical localization of PPARα in hepatocytes and cholangiocytes from both WT and cftr$^{-/-}$ mice showed similar diffuse staining, as shown in FIGS. 11A and 11B. Staining was mostly cytoplasmic although nuclear rim localization was observed. This principally cytoplasmic localization paralleled the distribution seen by western blot. Specificity demonstrated was demonstrated by omission of the primary antibody (FIGS. 11C and 11D). This distribution is similar to that observed in human liver (Dharancy et al., Gastroenterology, 128:334-342, 2005).

Figure 12:
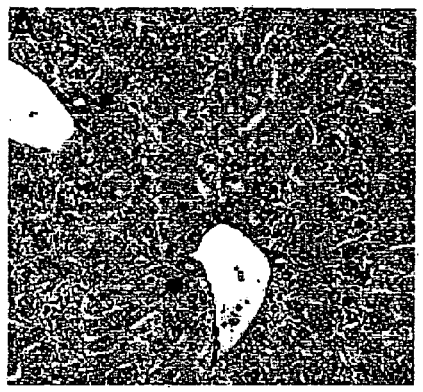
FIGS. 12 A-D are a series of photomicrographs showing the effect of DSS on liver histology in PPARα$^{-/-}$ mice and WT control mice. Representative hematoxylin and eosin-stained sections of liver are shown from PPARα$^{-/-}$ mice (FIG. 12A) and WT control mice (FIG. 12B), as well as from cftr$^{-/-}$ control mice (FIG. 12C). The portal tracts show normal appearing bile ducts (arrows). In cftr$^{-/-}$ mice treated with DSS (FIG. 12D), there is bile duct proliferation as indicated by the arrows with associated polymorphonuclear and mononuclear cell infiltrates highlighted by arrowheads. Magnification is 200×.
Figure 12:
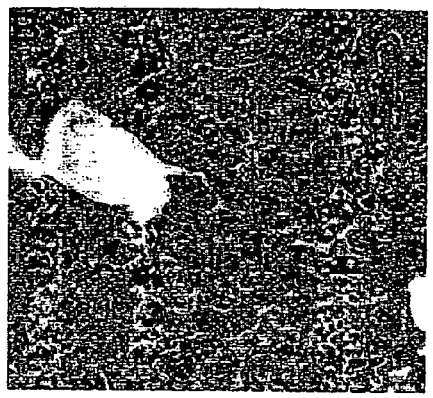
Figure 12:
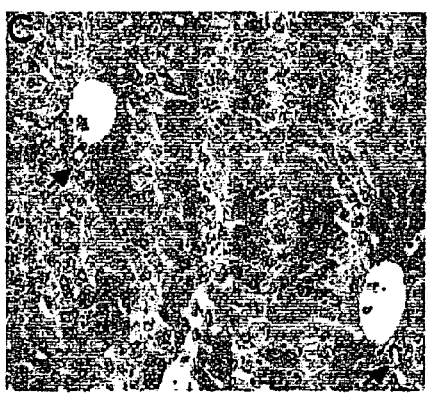
Figure 12:
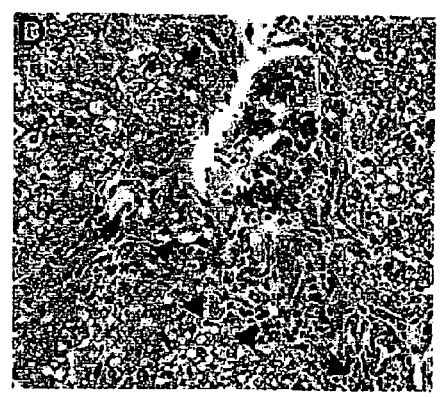

To test the hypothesis that an inability to increase PPARα in the liver upon DSS induced colitis is responsible for bile duct injury, liver histology from PPARα$^{-/-}$ mice following DSS induced colitis was examined. Administration of DSS led to a similar degree of bloody diarrhea in both PPARα$^{-/-}$ mice and WT controls. However, DSS did not induce bile duct injury in PPARα$^{-/-}$ mice (FIG. 12A) or controls (FIG. 12B). Cftr$^{-/-}$ mice in the absence of DSS (FIG. 12C) did not show bile duct injury, however when treated with DSS (FIG. 12D) showed periductular mononuclear cell infiltrates, some neutrophils, and bile duct proliferation.

Figure 13:
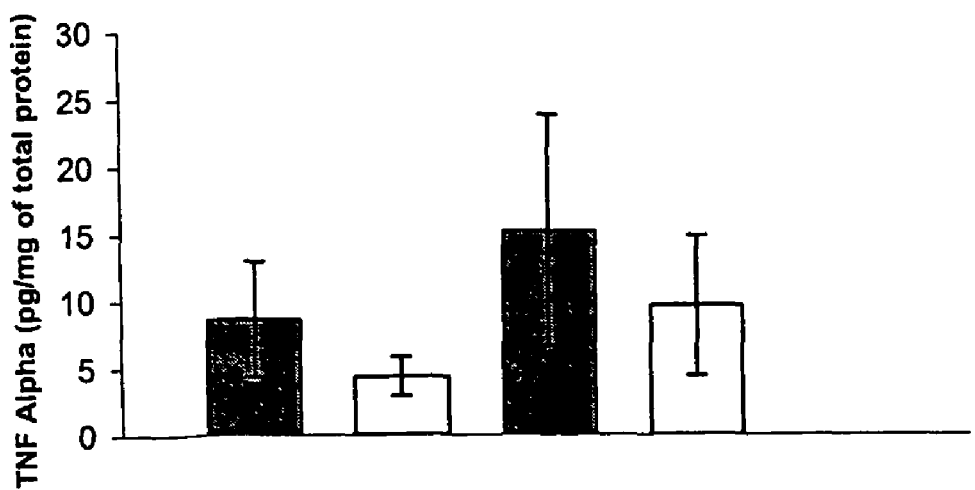
FIG. 13 is a bar graph showing TNFα levels in response to DSS. Liver TNFα levels were assayed in WT and cftr$^{-/-}$ mice. The Y-axis represents TNFα pg/mg of total protein. Results are expressed as ±SD. A minimum of 3 mice was used per group.

Since TNFα can suppress PPARα$^{-/-}$ expression in the liver, TNFα levels were examined as a function of DSS administration. As shown in FIG. 13, there was no statistically significant difference in liver TNFα levels comparing cftr$^{-/-}$ mice in the absence or presence of DSS (p=0.13). Similarly, there was no difference in TNFα levels comparing WT mice with or without administration of DSS (p=0.30).

Discussion

These results indicate that DSS induced bile duct injury in cftr$^{-/-}$ mice is associated with impaired PPARα expression. In WT mice, PPARα mRNA levels increased in the liver and were associated with nuclear translocation following induction of colitis. In contrast, neither an increase in PPARα mRNA nor nuclear translocation was observed in the liver of cftr$^{-/-}$ mice following induction of colitis. DHA, a known PPARα ligand (Lin et al., Biochemistry, 38:185-190, 1999), selectively increased mRNA expression of PPARα in cftr$^{-/-}$ mice. In contrast to PPARα, liver PPARγ levels were low in both WT and cftr$^{-/-}$ mice in the presence or absence of DHA and suppressed equally in both of these groups of animals by the induction of colitis. Colitis in mice does lead to decreased PPARγ expression in the colon (Bassaganya-Riera et al., Gastroenterology, 127:777-791, 2004; Katayama et al., Gastroenterology, 124:1315-1324, 2003) with our data showing a similar effect in the liver. However, this is unrelated to bile duct injury since WT mice demonstrate no biliary tract inflammation in contrast to cftr$^{-/-}$ mice.

These results are consistent with previous studies examining PPAR mRNA and protein expression in other inflammatory disorders. In addition to colitis, Dharancy et al. showed that PPARα mRNA levels are decreased in the livers of untreated patients with hepatitis C infection compared with controls, suggesting that low PPARα levels may play a role in the pathogenesis of chronic inflammation (Dharancy et al., supra). Functional studies as assessed by electrophoretic mobility shift assay of PPAR response element (PPRE) binding have been shown to parallel protein levels. For example, a recent study demonstrated that lipopolysaccharide decreased PPRE binding in the liver is associated with decreased PPARα and γ nuclear localization by western blot (Romics et al., Hepatology, 40:376-385, 2004). Another agonist of PPARα, WY14643, has recently been shown to increase PPARα mRNA levels in rat liver (Toyama et al., Biochem. Biophys. Res. Commun., 324:697-704, 2004). Based on these studies, impaired PPARα expression plays an important role in pathologic inflammation.

Much work has been done to understand how PPARs control inflammation. PPARα is expressed primarily in tissues with a high level of fatty acid catabolism such as liver, brown fat, kidney, heart, and skeletal muscle consistent with its role in lipid metabolism (Cabrero et al., Curr. Drug Targets Inflamm. Allergy, 1:243-248, 2002). It is also present in inflammatory cells such as macrophages and T lymphocytes (Marx et al., supra; Wahli et al., Chem Biol 2:261-266, 1995). Upon binding with a ligand, the cytosolic receptor translocates to the nucleus whereupon PPARs heterodimerize with Retinoid-X Receptor (RXR)α. The PPAR/RXR heterodimer binds to a DNA specific sequence called PPRE and stimulates transcription of target genes. PPARα activation results in the repression of NFκB signaling and inflammatory cytokine production in different cell-types. Consequently, PPARα agonists modulate mediators of inflammation such as NFκB, IL-6, and TNFα (Staels et al., supra; Cunard et al., J. Immunol. 169:6806-6812, 2002). The data shown herein indicate that in response to colitis, there is either a lack of ligand binding and/or a defect in the translocation process in cftr$^{-/-}$ mice. The differences in PPARα expression in these experiments likely play a role in regulating bile duct injury. However, it is possible that PPARα levels are decreased as a result of bile duct injury. This is supported by studies in rats whereby TNFα suppresses hepatic PPARα expression (Beier et al., FEBS Lett., 412:385-387, 1997). To test whether PPARα is down regulated in our model due to increased TNFα, we examined TNFα levels in WT and cftr$^{-/-}$ mice. Although similar trends were observed comparing WT and cftr$^{-/-}$ mice, there was no significant difference in TNFα levels in WT and cftr$^{-/-}$ mice with or without DSS treatment. Hence, this would not explain the decreased levels of PPARα seen in cftr$^{-/-}$ mice compared to WT controls. It would seem therefore, that the decrease in PPARα in cftr$^{-/-}$ associated bile duct injury is not secondary to the inflammatory response itself, but may play an important role in mediating the injury.

In addition to their role in suppressing inflammation, PPARs are known to regulate lipid metabolism. CF in both humans (Freedman et al., (2004), supra) and in mouse models (Freedman et al., (1999), supra) is associated with a defect in fatty acid metabolism, specifically an increase in AA and a reciprocal decrease in DHA. Since administration of high doses of DHA to cftr$^{-/-}$ mice ameliorates the pathology in CF affected tissues (Freedman et al., (1999), supra) including the bile duct injury in response to DSS induced colitis in our CF mouse model (Blanco et al., supra), we examined whether DHA may mediate its action, in part through PPAR. DHA is a known PPARα agonist and the requirement for doses of DHA beyond what is needed to correct the fatty acid defect suggests that it may decrease inflammation through modulation of inflammatory mediators. The results presented herein demonstrate that DHA can increase PPARα mRNA levels, and this may at least in part explain its mechanism to ameliorate bile duct injury. However, the fact that DHA did not induce translocation of PPARα in the liver of cftr$^{-/-}$ mice suggests that DHA may have other actions including direct activation of Retinoid-X Receptor (de Urquiza et al., Science, 290:2140-2144, 2000). In addition, this does not preclude the possibility that the full effect of DHA involves other pathways including modulation of prostanoids (Freedman et al., J. Appl. Physiol., 92:2169-2176, 2002).

The mechanism by which CFTR dysfunction and low PPARα expression leads to bile duct injury may involve a combination of an impaired PPARα response together with other aspects of CFTR dysfunction, such as altered intestinal flora. In the CF lung, there is an aberrant immune response in the setting of altered bacterial flora, leading to chronic lung disease. Similarly, bacterial overgrowth in the CF intestine, as recently shown in the cftr$^{-/-}$ mouse (Norkina et al., Infect. Immun., 72:6040-6049, 2004), may play a role in predisposing to excessive inflammation. In the setting of colitis and altered bacterial flora, the combination of CF associated bacterial pathogens in portal blood and abnormal qualitative and/or quantitative innate immune responses in the liver, accompanied by a difference in cytokines/chemokines may predispose to bile duct injury in cftr$^{-/-}$ mice. This mechanism potentially explains why cftr$^{-/-}$ mice develop bile duct injury in the setting of colitis whereas WT mice do not. It is clear from the current study that a decrease in PPARα is not sufficient to cause bile duct injury, as PPARα$^{-/-}$ mice did not develop bile duct injury in the setting of colitis. Rather, it appears that the combination of an impaired PPARα response together with other aspects of CFTR dysfunction, such as altered intestinal flora, may be critical.

Example 8

PPARα Expression is Decreased in Macrophages from cftr$^{-/-}$ Mice

We have shown that peritoneal macrophages from CF mice have decreased PPAR as well as an increased NFκB activity. These are normalized by pretreatment with the n-3 fatty acid DHA. DHA's actions could be through its PPAR agonist effect or alternatively through a downregulation of proinflammatory arachidonic acid metabolites. The aim of this study was to determine if TNFα and IL-6 secretion is increased in CF peritoneal macrophages and whether it is normalized by selective PPAR agonists. Furthermore we wanted to relate this to the fatty acid profile of CF macrophages.

Methods

Cftr$^{-/-}$ exon 10 knockout mice and wild-type (WT) littermates were maintained on peptamen (as described above). Peritoneal macrophages were induced by intraperitoneal injection of 2 ml thioglycollate broth followed by harvesting of the macrophages 4 days after injection. For studies determining the effect of in vivo pretreatment of DHA, cftr$^{-/-}$ mice were given 40 mg DHA/day for 10 days. For in vitro experiments, harvested macrophages were plated in RPMI medium with 10% serum and incubated for 12 hours with media alone or with DHA (5 μM), EPA (5 μM) the PPAR agonist Wy14643 (50 μM) or the PPAR agonist rosiglitazone (10 μM). The cells were washed and then stimulated with 0-10000 ng/ml LPS for 4.5 hours. TNFα and IL-6 secretion were measured by ELISA. Fatty acids were analyzed by GC/MS.

Results

Figure 14:
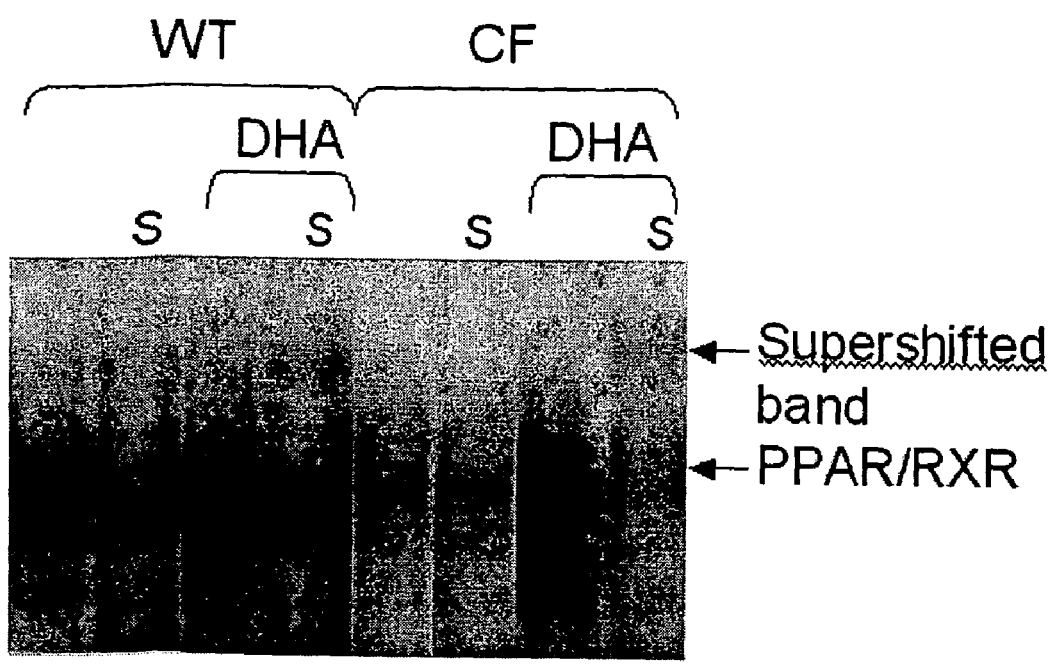
FIG. 14 is an electrophoretic mobility shift assay (EMSA) showing that PPAR/RXR binding to the PPAR response element is reduced in cftr$^{-/-}$ cells but can be normalized by DHA treatment.

Electrophoretic mobility shift assays showed that PPARα/RXR binding to the PPAR response element is reduced in cftr$^{-/-}$ mice but can be normalized by DHA treatment (FIG. 14).

Figure 15:
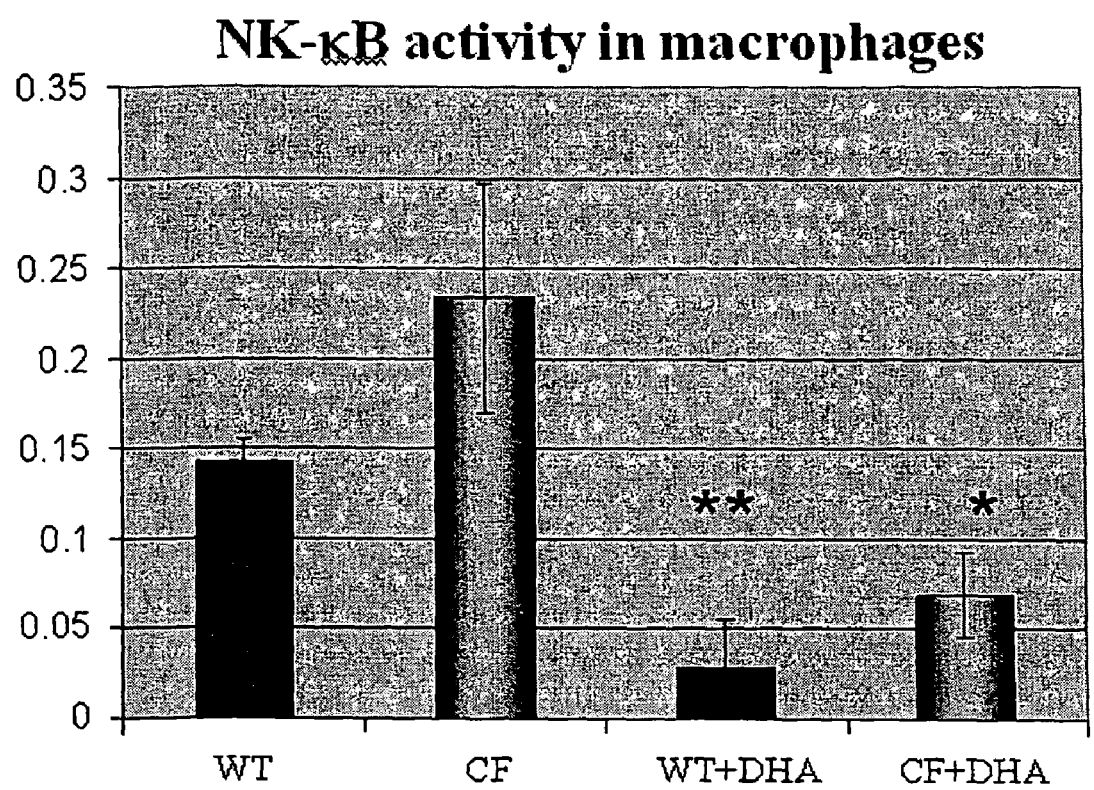
FIG. 15 is a bar graph showing the increase in NFκB activity in macrophages from cftr$^{-/-}$ mice. Oral DHA treatment decreased the activity in both wild-type and cftr-/- macrophages (*p<0.05, ** p<0.01).

Furthermore, in cftr$^{-/-}$ mice, NF-κB activity was increased in peritoneal macrophages from cftr$^{-/-}$ mice as compared to wild type. Oral treatment with DHA decreased the activity in both wild type and cftr$^{-/-}$ macrophages (FIG. 15).

Figure 16:
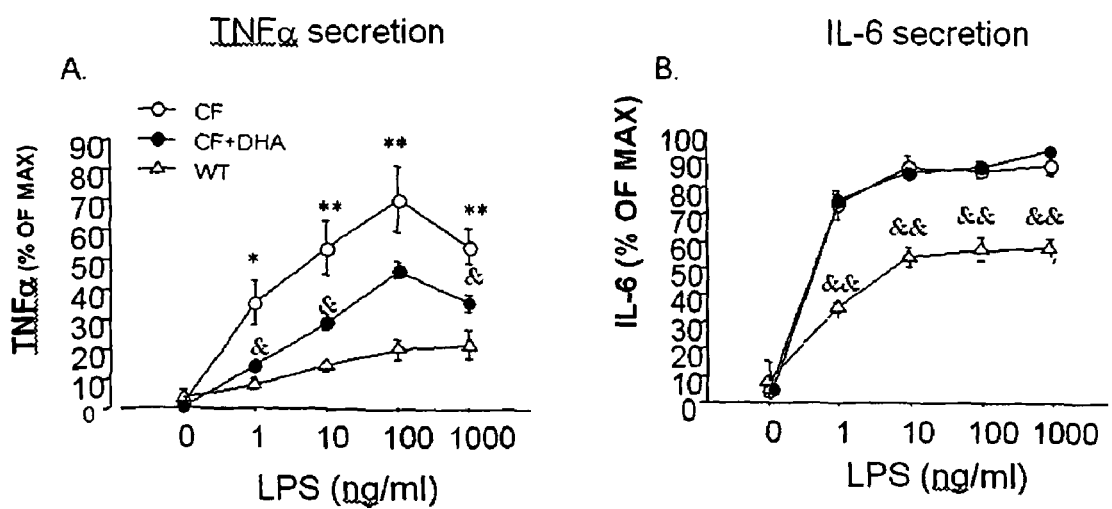
FIGS. 16A and 16B are graphs showing DHA treatment in vivo decreased LPS-induced TNFα secretion (FIG. 16A) but not IL-6 secretion in CF mouse peritoneal macrophages. (*, ** p<0.05, 0.01 compared with wild type and &, && p<0.05, 0.01 compared with CF).
Figure 17:
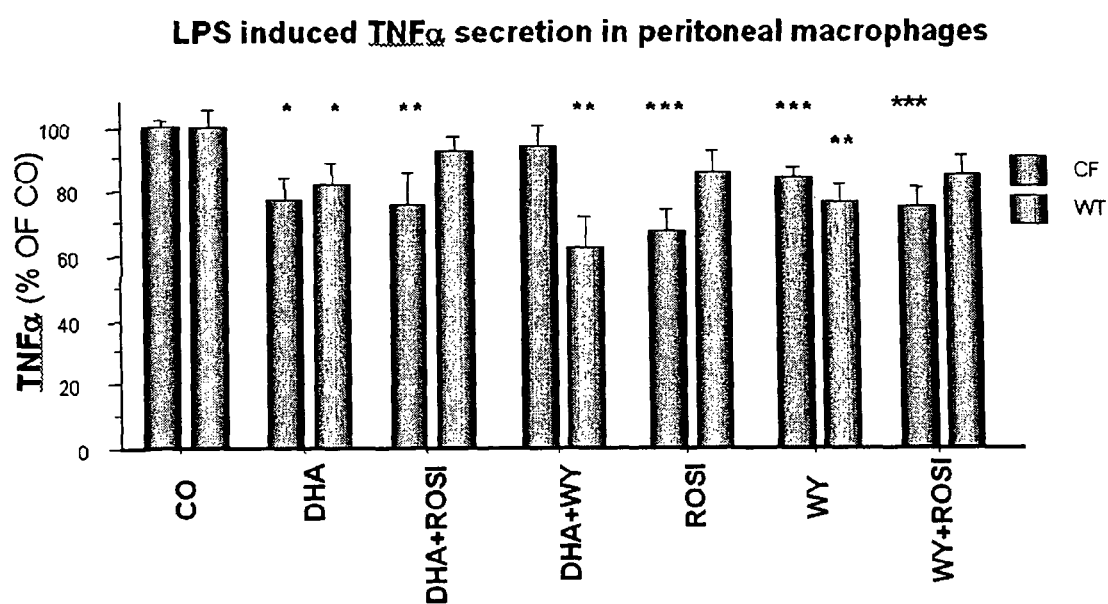
FIG. 17 is a bar graph showing the effect of PPAR agonists on TNFα secretion in peritoneal macrophages from LPS-induced wild-type and CFTR$^{-/-}$ mice. Values are normalized to secretion in controls stimulated with 100 ng/ml LPS (defined as m100%). Incubating the cells with DHA in vitro produced results similar to DHA pretreatment of the CF mice. A combination of DHA and either WY14643 or rosiglitazone did not further decrease secretion of TNFα. Wy14643 decreased TNFα secretion in CF macrophages by 16% ($p<0.001$) and the PPARγ agonist rosiglitazone decreased TNFα secretion by 33% ($p<0.001$). A combination of the PPARα and PPARγ agonists had no additive effect on TNFα secretion.
Figure 18:
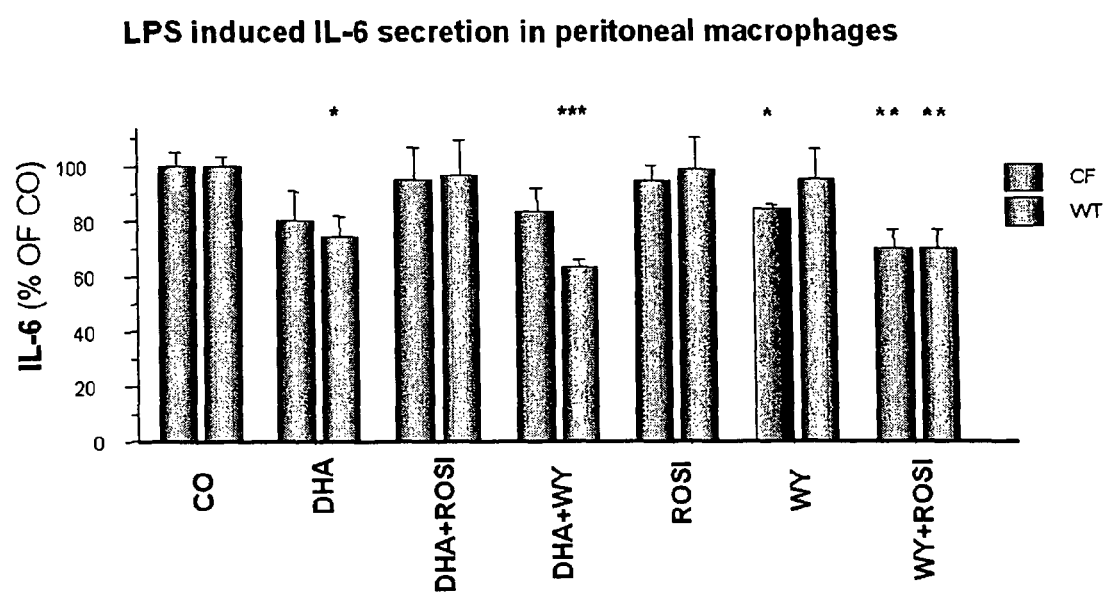
FIG. 18 is a bar graph showing the effect of PPAR agonists on IL-6 secretion in peritoneal macrophages from LPS-induced wild type and cftr$^{-/-}$ mice. Values are normalized to secretion in controls stimulated with 100 ng/ml LPS (defined as 100%). Il-6 secretion was decreased by 16% ($p<0.05$) by Wy14643 in CF macrophages, with rosiglitazone having no effect on IL-6 secretion. Wy14643 and rosiglitazone together decreased Il-6 secretion by an additional 13% ($p<0.05$) compared with Wy14643 alone.

LPS stimulation of CF peritoneal macrophages led to an increase in both TNFα (3.1 fold) and IL-6 (2.3 fold) secretion compared to that seen from WT macrophages (FIGS. 16A and B). Pretreatment of CF mice with oral DHA decreased TNFα secretion from peritoneal macrophages by 43% (p<0.05), with no effect on IL-6 secretion. Similar results were seen after incubation of CF macrophages in vitro with DHA (FIG. 17). The n-3 fatty acid eicosapentaenoic acid (EPA) had no effect on TNFα secretion indicating a specific effect of DHA unrelated to decreases in the n-6 arachidonate pathway. The PPARα agonist Wy14643 decreased LPS induced TNFα secretion in CF macrophages by 27% (p<0.01) (FIG. 17) and the PPARγ agonist rosiglitazone decreased TNFα secretion by 28% (p<0.001) (FIG. 17), with neither affecting IL-6 secretion (FIG. 18). The effect of DHA and Wy14643 were specific for CF in that these agonists did not alter secretion from WT macrophages. In contrast, rosiglitazone also affected WT macrophages with a decrease in TNFα secretion by 18%. (p<0.05). Fatty acid analysis demonstrated a selective increase in the arachidonate downstream product 22:5n-6 in the CF macrophages (0.26 mol % compared to 0.42, p<0.05)(Table 1).

TABLE 1

Fatty acid profile in peritoneal macrophages.

|  | WT | CF |
|---|---|---|
| 16:0 | 31.3 ± 0.9 | 29.4 ± 0.9 |
| 18:0 | 18.1 ± 0.5 | 18.2 ± 1.0 |
| 18:1 n-9 | 11.8 ± 0.4 | 13.6 ± 1.3 |
| n-6 |  |  |
| 18:2 | 11.8 ± 0.8 | 10.9 ± 0.5 |
| 20:3 | 1.8 ± 0.06 | 1.7 ± 0.11 |
| 20:4 (AA) | 13.5 ± 0.6 | 14.4 ± 0.6 |
| 22:4 | 3.8 ± 0.3 | 4.1 ± 0.3 |
| 22:5 | 0.26 ± 0.02 | 0.42 ± 0.07* |
| n-3 |  |  |
| 18:3 | 0.23 ± 0.09 | 0.21 ± 0.08 |
| 20:5 | 0.26 ± 0.10 | 0.23 ± 0.03 |
| 22:5 | 1.6 ± 0.14 | 1.8 ± 0.15 |
| 22:6 (DHA) | 2.4 ± 0.3 | 2.9 ± 0.3 |

Conclusion

LPS induced TNFα and IL-6 secretion was increased in CF peritoneal macrophages with TNFα secretion being selectively decreased by treatment with DHA as well as the PPAR agonist Wy14643. The effect of rosiglitazone on the inhibition of TNFα secretion appears to be unrelated to CFTR in that it was observed in both WT and CF macrophages. The fact that Wy14643 only had an effect in the CF macrophages is consistent with the hypothesis that a defect PPARα is at least partly responsible for the increase in TNFα secretion. This is further supported by the data demonstrating that DHA is decreasing TNFα secretion through its actions as a PPAR agonist and not by affecting the n-6 arachidonate pathway based on normal DHA and arachidonate levels as well as the lack of effect of EPA.

Example 9

Expression of LXR is Decreased in Macrophages from CFTR$^{-/-}$ Mice

Figure 19:
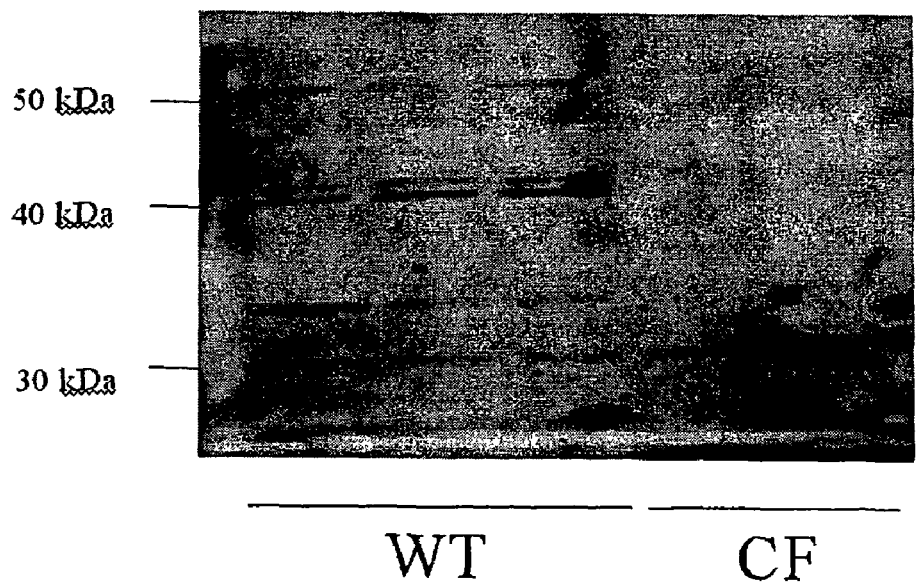
FIG. 19 is a western blot showing the decrease in LXR (40 kDa) in cftr$^{-/-}$ macrophages compared with wild-type macrophages.

PPARs exert their effects largely through binding to RXR in the nucleus. LXR is another member of the family of nuclear receptors and also binds to RXR and downregulates inflammation as well as activates lipid metabolism including cholesterol efflux. To determine expression of LXR in macrophages in the absence of CFTR, peritoneal macrophages were prepared from both wild-type and cftr$^{-/-}$ mice. Equal amounts of protein were run on this SDS polyacrylamide gel. Western blotting was performed using an antibody again LXRα. As can be seen in FIG. 19, LXR (40 kDa) is markedly diminished in cftr$^{-/-}$ macrophages (2 samples) compared with wild-type controls.

Therapeutic Compounds

We have discovered that changes in PPARs, specifically PPARγ and PPARα, expression and activity occur in tissues specifically regulated by CFTR. Non-limiting examples of the therapeutic compounds useful in the methods of the invention include agonists or inducers of PPARs, including PPARγ, PPARα, PPARδ, or any combination thereof. (See Forman et al., Proc. Natl. Acad. Sci. 94:4312-4317, 1997 for a list of some of these compounds). For example, agonists of PPARα include DHA, Wy14643, and fibrates (e.g., bezafibrate and bezafibrate analogs such as binifibrate, ciprofibrate, clinofibrate, clofibrate, etofibrate; fenofibrate, and gemfibrozil. Agonists of PPARγ include any of the thiazolidinediones, such as balaglitazone, ciglitazone, englitazone, rosiglitazone, darglitazone, englitazone, netoglitazone, KRP-297, JTT-501, NC-2100, NIP-223, MCC-555, L-764486, CS-011, GI262570, GW347845, or FK614. Preferred thiazolidinediones useful as PPARγ agonists include pioglitazone and any analogs thereof (Actos, Takeda Pharmaceuticals, described, for example, in U.S. Pat. Nos. 4,687,777; 5,965,584; 6,150,383; 6,150,384; 6,166,043; 6,172,090; 6,211,205; 6,271,243; 6,303,640; and 6,329,404), rosiglitazone and analogs thereof (Avandia, GlaxoSmithKline, described for example, in U.S. Pat. Nos. 5,002,953, 5,741,803, and 6,288,095), and troglitazone, and any analogs thereof. Agonists can also include tyrosine-based PPARγ modulators (e.g., fluoromethyloxycarbonyl, GI262570; [(S)-2-(2-benzoylphenylamino)-3-[4-[2-(5-methyl-2-phenyl-2-oxazol-4-yl)ethoxy]phenyl]propionic acid, and GW347845 (Cobb et al., J Med Chem. 41:5055-5069, 1998)), 3-(2,4-dichlorobenzyl)-2-methyl-N-(pentylsulfonyl)-3H-benzimidazole-5-carboxamide (FK614)). Additional PPARγ agonists include prostaglandin J2 and nonsteroidal anti-inflammatory drugs such as indomethacin, ibuprofen, and fenoprofen. Other PPAR agonists, including dual PPARα/PPARγ agonists, that may be used in the methods, of the invention are AA-10090, AD-5075, AMG-131, ARH-049020, AR-H039242 (AstraZeneca), AVE-0847, AVE-8134, AY-31637, BAY-549801, bexarotene, BM-131246, BM-501050, CLX-0921, CLX-0940, DRF-10945, DRF-4832, E-3030, farglitazar, fenofibrate/metformin, GW-0072, GW-1929, GW-2570, GW-409544 (Glaxo-Wellcome), GW-409890, GW-501516, GW-5393, GW-590735, GW-7282, GW-9578, KRP-101, KRP297 (Kyorin Merck), KT-6207, L-764406, LF-200337, LG-101506, LR-90, LY-465608, LY-510929, LY-518674, MBX-102, MK-0767, muraglitazar, naveglitazar, NC-2100, NS-220, ONO-5129, oxeglitazar, PD-72953, R-119702, ragaglitazar, reglitazar, SB-219994, tesaglitazar, 641597, and TY-51501. For additional descriptions of dual PPARα/PPARγ agonists see U.S. Pat. No. 6,414,002 and Murakami et al., Diabetes 47:1841-1847, 1998.

Combinations of any of these therapeutic compounds are also contemplated by the invention. For example, a combination of a thiazolidinediones, such as rosiglitazone or pioglitazone, with a non-steroidal anti-inflammatory drug or an anti-oxidant can be used in the methods of the invention.

The therapeutic compounds of the invention may act as an agonist or an inducer of either PPARγ or PPARα or and PPARγ- or PPARα-like receptors, or any combination thereof. It will be recognized by the skilled artisan that although a compound may be classified as a regulator of PPARγ or PPARα, this classification is not intended to be limiting. The compound may affect both pathways and may also affect additional pathways. For example, DHA is a PPARα agonist but can also act as a stimulator of PPARγ activity.

Inducers of PPAR include any compound that increases the biological activity or expression level of any one or more PPAR genes. For example, there are a variety of natural and synthetic ligands exist that cause PPARγ activation. For example, arachidonic acid metabolites including prostaglandin J2 and hydroxyoctadecanoic acid as well as α-linolenic acid, eicosapentaenoic acid (EPA; C20:5n-3), and DHA stimulate PPARγ activity. DHA is synthesized in peroxisomes through beta oxidation and, because PPARγ influences beta oxidation, it is likely that PPARγ induction increases DHA synthesis within the cells (see below). Therefore, the low DHA and PPAR levels could be due to either low PPAR expression leading to low DHA synthesis in peroxisomes. Alternatively, low DHA levels results in decreased PPAR activation, thereby decreasing PPAR expression. It should be noted, however, that DHA is a more potent ligand for PPARα than for PPARγ.

Additional therapeutic compounds useful in the methods of the invention include any LXR agonists. Examples of LXR agonists include GW3965 and T0901317 (Cayman Chemical Co., Ann Arbor, Mich.). T0901317 is a highly selective LXR agonist that has been shown both in vitro and in vivo to regulate LXR target genes such as ABCA1. See, for example, Chisholm, J., Lipid Res. 44:2039-2048, 1996; Joseph et al., Proc. Natl. Acad. Sci. USA. 99: 7604-7609, 2002; Wu et al., J. Biol. Chem. 278:15565-15570, 2003; and Zaghini et al, J. Biol. Chem. 277:1324-1331, 2002.

DHA Reduces Pathology in CF Mice

Docosahexaenoic acid (DHA) levels are decreased in plasma of cystic fibrosis patients (Roulet et al., Eur. J. Pediatr. 156: 952-956, 1997) as well as in CFTR regulated tissues from cftr$^{-/-}$ mice (Freedman et al., Proc. Natl. Acad. Sci. USA 96: 13995-14000, 1999). Docosahexaenoic acid biosynthesis requires a beta-oxidation step which occurs in peroxisomes. Since PPARs regulate the expression of acyl coenzyme-A oxidase gene, a key element in fatty acid β-oxidation, a deficit in PPARγ expression would produce an alteration in peroxisomal function possibly resulting in low docosahexaenoic acid levels.

Dietary DHA supplementation of cftr$^{-/-}$ mice increases phospholipids-bound DNA levels in the blood and reduces lung inflammation following a *Pseudomonas* LPS challenge as measured by the neutrophil concentration in a bronchoalveolar lavage (BAL). No significant effects on TNFα, MIP-2, or KC were measured. Instead, a selective decrease in the eicosanoids PGE$_2$, 6-keto-PGF$_{1\alpha}$, PGF$_{2\alpha}$, and thromboxane B$_2$. PGE2 is a potent neutrophil chemoattractant and its reduction underlies the reduced neutrophil recruitment into the lung following the LPS challenge.

DHA also inhibits apoptosis in tissues normally expressing high CFTR levels. For example, DHA treatment decreases villi height in the ileum of cftr$^{-/-}$ mice.

The loss of ion channel function is also mitigated by DHA treatment. DHA, at nanomolar concentrations, activate fast sodium channels (plasma membrane) and calcium channels (sarcoplasmic reticulum) in cardiac myocytes. Additionally, in T84 colon cancer cells, DHA enhances carbachol-stimulated chloride conductance without affecting cAMP-stimulated chloride conductance.

Identification of Candidate Compounds

A candidate compound that is beneficial in the treatment (reduction or prevention of symptoms) caused by a mutation in the CFTR gene can be identified by the methods of the present invention. A candidate compound can be identified for its ability to affect the biological activity of a PPAR or the expression of a PPAR gene. While the exemplary methods described below refer to PPARγ, it will be understood that the methods can be used as screening assays to identify compounds that promote the expression or biological activity of any PPAR gene or protein.

Any number of methods are available for carrying out screening assays to identify new candidate compounds that promote the expression of a PPARγ gene. In one example, candidate compounds are added at varying concentrations to the culture medium of cultured cells expressing a PPARγ gene. Gene expression is then measured, for example, by microarray analysis, northern blot analysis (see, for example, *Short Protocols in Molecular Biology*, ed. Ausubel, et al., (1989)), or RT-PCR, using any appropriate fragment prepared from the PPARγ nucleic acid molecule as a hybridization probe. The level of PPARγ gene expression in the presence of the candidate compound is compared to the level measured in a control culture medium lacking the candidate compound. A compound which promotes an increase in the expression of a PPARγ gene is considered useful in the invention and may be used as a therapeutic to treat a human patient.

In another example, the effect of candidate compounds may be measured at the level of PPARγ protein production using standard immunological techniques, such as western blotting or immunoprecipitation with an antibody specific for the PPARγ protein. Polyclonal or monoclonal antibodies that are capable of binding to a PPARγ protein may be used in any standard immunoassay format (e.g., ELISA, western blot, or RIA assay) to measure the level of the protein. In some embodiments, a compound that promotes an increase in PPARγ expression or biological activity is considered particularly useful.

Expression of a reporter gene that is operably linked to a PPARγ promoter can also be used to identify a candidate compound for treating a disease associated with a CFTR mutation. Assays employing the detection of reporter gene products are extremely sensitive and readily amenable to automation, hence making them ideal for the design of high-throughput screens. Assays for reporter genes may employ, for example, calorimetric, chemiluminescent, or fluorometric detection of reporter gene products. Many varieties of plasmid and viral vectors containing reporter gene cassettes are easily obtained. Such vectors contain cassettes encoding reporter genes such as lacZ/β-galactosidase, green fluorescent protein, and luciferase, among others. A genomic DNA fragment carrying a PPARγ-specific transcriptional control region (e.g., a promoter and/or enhancer) is first cloned using standard approaches (such as those described by Ausubel et al., supra). The DNA carrying the PPARγ transcriptional control region is then inserted, by DNA subcloning, into a reporter vector, thereby placing a vector-encoded reporter gene under the control of the PPARγ transcriptional control region. The activity of the PPARγ transcriptional control region operably linked to the reporter gene can then be directly observed and quantified as a function of reporter gene activity in a reporter gene assay.

In one embodiment, for example, the PPARγ transcriptional control region could be cloned upstream from a luciferase reporter gene within a reporter vector. This could be introduced into the test cells, along with an internal control reporter vector (e.g., a lacZ gene under the transcriptional regulation of the β-actin promoter). After the cells are exposed to the test compounds, reporter gene activity is measured and PPAR-γ reporter gene activity is normalized to internal control reporter gene activity.

A candidate compound identified by the methods of the present invention can be from natural as well as synthetic sources. Those skilled in the field of drug discovery and development will understand that the precise source of test extracts or compounds is not critical to the methods of the invention. Examples of such extracts or compounds include, but are not limited to, plant-, fungal-, prokaryotic-, or animal-based extracts, fermentation broths, and synthetic compounds, as well as modification of existing compounds. Numerous methods are also available for generating random or directed synthesis (e.g., semi-synthesis or total synthesis) of any number of chemical compounds, including, but not limited to, saccharide-, lipid-, peptide-, and nucleic acid-based compounds. Synthetic compound libraries are commercially available from Brandon Associates (Merrimack, N.H.) and Aldrich Chemical (Milwaukee, Wis.). Alternatively, libraries of natural compounds in the form of bacterial, fungal, plant, and animal extracts are commercially available from a number of sources, including Biotics (Sussex, UK), Xenova (Slough, UK), Harbor Branch Oceangraphics Institute (Ft. Pierce, Fla.), and PharmaMar, U.S.A. (Cambridge, Mass.). In addition, natural and synthetically produced libraries are produced, if desired, according to methods known in the art, e.g., by standard extraction and fractionation methods. Furthermore, if desired, any library or compound is readily modified using standard chemical, physical, or biochemical methods.

Administration of Therapeutics

The present invention also includes the administration of a PPAR inducer, PPAR agonist, an antioxidant, or any combination thereof, for the treatment of a disease associated with a CFTR mutation. Therapeutics of this invention may be formulated as pharmaceutically acceptable salts may include non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acids such as hydrochloric acid, hydrobromic acid, sulfuric acid phosphoric acid, or the like. Metal complexes include zinc, iron, and the like. One exemplary pharmaceutically acceptable carrier is physiological saline. Other physiologically acceptable carriers and their formulations are known to one skilled in the art and described, (see, e.g., Remington: The Science and Practice of Pharmacy, 20th edition, 2000, ed. A. R. Gennaro, Lippincott Williams & Wilkins, Philadelphia, and Encyclopedia of Pharmaceutical Technology, eds. J. Swarbrick and J. C. Boylan, 1988-1999, Marcel Dekker, New York).

Pharmaceutical formulations of a therapeutically effective amount of a compound of the invention, or pharmaceutically acceptable salt-thereof, can be administered orally, parenterally (e.g. intramuscular, intraperitoneal, intravenous, or subcutaneous injection), topically, locally, or by intrathecal or intracerebroventricular injection in an admixture with a pharmaceutically acceptable carrier adapted for the route of administration.

Methods well known in the art for making formulations are found, for example, in Remington: The Science and Practice of Pharmacy, 20th edition, 2000, ed. A. R. Gennaro, Lippincott Williams & Wilkins, Philadelphia. Compositions intended for oral use may be prepared in solid or liquid forms according to any method known to the art for the manufacture of pharmaceutical compositions. The compositions may optionally contain sweetening, flavoring, coloring, perfuming, and/or preserving agents in order to provide a more palatable preparation. Solid dosage forms for oral administration include capsules, tablets, pills, powders, and granules. In such solid forms, the active compound is admixed with at least one inert pharmaceutically acceptable carrier or excipient. These may include, for example, inert diluents, such as calcium carbonate, sodium carbonate, lactose, sucrose, starch, calcium phosphate, sodium phosphate, or kaolin. Binding agents, buffering agents, and/or lubricating agents (e.g., magnesium stearate) may also be used. Tablets and pills can additionally be prepared with enteric coatings.

Liquid dosage forms for oral administration include pharmaceutically acceptable emulsions, solutions, suspensions, syrups, and soft gelatin capsules. These forms contain inert diluents commonly used in the art, such as water or an oil medium. Besides such inert diluents, compositions can also include adjuvants, such as wetting agents, emulsifying agents, and suspending agents.

Formulations for parenteral administration include sterile aqueous or non-aqueous solutions, suspensions, or emulsions. Examples of suitable vehicles include propylene glycol, polyethylene glycol, vegetable oils, gelatin, hydrogenated naphalenes, and injectable organic esters, such as ethyl oleate. Such formulations may also contain adjuvants, such as preserving, wetting, emulsifying, and dispersing agents. Biocompatible, biodegradable lactide polymer, lactide/glycolide copolymer, or polyoxyethylene-polyoxypropylene copolymers may be used to control the release of the compounds. Other potentially useful parenteral delivery systems for the proteins of the invention include ethylene-vinyl acetate copolymer particles, osmotic pumps, implantable infusion systems, and liposomes.

Liquid formulations can be sterilized by, for example, filtration through a bacteria-retaining filter, by incorporating sterilizing agents into the compositions, or by irradiating or heating the compositions. Alternatively, they can also be manufactured in the form of sterile, solid compositions which can be dissolved in sterile water or some other sterile injectable medium immediately before use.

The amount of active ingredient in the compositions of the invention can be varied. One skilled in the art will appreciate that the exact individual dosages may be adjusted somewhat depending upon a variety of factors, including the protein being administered, the time of administration, the route of administration, the nature of the formulation, the rate of excretion, the nature of the subject's conditions, and the age, weight, health, and gender of the patient. Generally, dosage levels of between 0.1 μg/kg to 100 mg/kg of body weight are administered daily as a single dose or divided into multiple doses. Desirably, the general dosage range is between 250 μg/kg to 5.0 mg/kg of body weight per day. Wide variations in the needed dosage are to be expected in view of the differing efficiencies of the various routes of administration. For instance, oral administration generally would be expected to require higher dosage levels than administration by intravenous injection. Variations in these dosage levels can be adjusted using standard empirical routines for optimization, which are well known in the art. In general, the precise therapeutically effective dosage will be determined by the attending physician in consideration of the above-identified factors.

The therapeutics of the invention can be administered in a sustained release composition, such as those described in, for example, U.S. Pat. No. 5,672,659 and U.S. Pat. No. 5,595,760. The use of immediate or sustained release compositions depends on the type of condition being treated. If the condition consists of an acute or subacute disorder, a treatment with an immediate release form will be preferred over a prolonged release composition. Alternatively, for preventative or long-term treatments, a sustained released composition will generally be preferred.

Gene Therapy

Gene therapy is another therapeutic approach for increasing PPAR biological activity. Heterologous nucleic acid molecules encoding a PPAR protein can be delivered to the affected cells (e.g., lung epithelium). Expression of PPARγ proteins in the target cells can ameliorate the symptoms associated with CFTR dysfuntion. The nucleic acid molecules must be delivered to those cells in a form in which they can be taken up by the cells and so that sufficient levels of protein can be produced to increase the PPAR biological activity.

Transducing viral (e.g., retroviral, adenoviral, and adeno-associated viral) vectors can be used for somatic cell gene therapy, especially because of their high efficiency of infection and stable integration and expression (see, e.g., Cayouette et al., Human Gene Therapy 8:423-430, 1997; Kido et al., Current Eye Research 15:833-844, 1996; Bloomer et al., Journal of Virology 71:6641-6649, 1997; Naldini et al., Science 272:263-267, 1996; and Miyoshi et al., Proc. Natl. Acad. Sci. U.S.A. 94:10319, 1997). For example, a full length PPAR gene, or a portion thereof, can be cloned into a retroviral vector and expression can be driven from its endogenous promoter, from the retroviral long terminal repeat, or from a promoter specifically expressed in a target cell type of interest. Other viral vectors that can be used include, for example, a vaccinia virus, a bovine papilloma virus, or a herpes virus, such as Epstein-Barr Virus (also see, for example, the vectors of Miller, Human Gene Therapy 15-14, 1990; Friedman, Science 244:1275-1281, 1989; Eglitis et al., BioTechniques 6:608-614, 1988; Tolstoshev et al., Current Opinion in Biotechnology 1:55-61, 1990; Sharp, Lancet 337:1277-1278, 1991; Cornetta et al., Nucleic Acid Research and Molecular Biology 36:311-322, 1987; Anderson, Science 226:401-409, 1984; Moen, Blood Cells 17:407-416, 1991; Miller et al., Biotechnology 7: 980-990, 1989; Le Gal La Salle et al., Science 259:988-990, 1993; and Johnson, Chest 107:77S-83S, 1995). Retroviral vectors are particularly well developed and have been used in clinical settings (Rosenberg et al., N. Engl. J. Med. 323:370, 1990; Anderson et al., U.S. Pat. No. 5,399,346). Most preferably, a viral vector is used to administer the gene of interest to a target endothelial cell.

Non-viral approaches can also be employed for the introduction of therapeutic nucleic acids to a cell of a patient. For example, a nucleic acid molecule can be introduced into a cell by administering the nucleic acid in the presence of lipofection (Felgner et al., Proc. Natl. Acad. Sci. U.S.A. 84:7413, 1987; Ono et al., Neuroscience Letters 17:259, 1990; Brigham et al., Am. J. Med. Sci. 298:278, 1989; Staubinger et al., Methods in Enzymology 101:512, 1983), asialoorosomucoid-polylysine conjugation (Wu et al., J. Biol. Chem. 263: 14621, 1988; Wu et al., J. Biol. Chem. 264:16985, 1989), or by micro-injection under surgical conditions (Wolff et al., Science 247:1465, 1990). Preferably the nucleic acids are administered in combination with a liposome and protamine.

Gene transfer can also be achieved using non-viral means involving transfection in vitro. Such methods include the use of calcium phosphate, DEAE dextran, electroporation, and protoplast fusion. Liposomes can also be potentially beneficial for delivery of DNA into a cell. Transplantation of normal genes into the affected tissues of a patient can also be accomplished by transferring a normal nucleic acid into a cultivatable cell type ex vivo (e.g., an autologous or heterologous primary cell or progeny thereof), after which the cell (or its descendants) are injected into a targeted tissue.

cDNA expression for use in gene therapy methods can be directed from any suitable promoter (e.g., an endocan promoter, Flt-1 promoter, or other tumor endothelial promoter identified using methods known in the art), and regulated by any appropriate mammalian regulatory element (see for example Davis et al. (1986) *Basic Methods In Molecular Biology,* Maniatis et al. *Molecular Cloning: A Laboratory Manual,* 2nd Edition (1989), and Short Protocols in Molecular Biology, ed. Ausubel, et al., (1989)). For example, if desired, an enhancers known to preferentially direct gene expression in a tumor endothelial cell, (e.g., the 300 base pair Tie-2 intronic enhancer element described herein) can be used to direct the expression of a nucleic acid. The enhancers used can include, without limitation, those that are characterized as tissue- or cell-specific enhancers. Alternatively, if a genomic clone is used as a therapeutic construct, regulation can be mediated by the cognate regulatory sequences or, if desired, by regulatory sequences derived from a heterologous source, including any of the promoters or regulatory elements described above.

Another therapeutic approach included in the invention involves administration of a recombinant nuclear encoded mitochondrial metabolism or proteasomal polypeptide, either directly to the site of a potential or actual disease-affected tissue (for example, by injection into the ventricles of the brain or into the cerebrospinal fluid) or systemically (for example, by any conventional recombinant protein administration technique). The dosage of the administered protein depends on a number of factors, including the size and health of the individual patient. For any particular subject, the specific dosage regimes should be adjusted over time according to the individual need and the professional judgment of the person administering or supervising the administration of the compositions. Generally, between 0.1 mg and 100 mg, is administered per day to an adult in any pharmaceutically acceptable formulation.

OTHER EMBODIMENTS

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method for treating a disease in a human patient, wherein said patient has a mutation in the CFTR gene and wherein said mutation is associated with said disease, said method comprising administering to said patient a therapeutically effective amount of a peroxisome proliferator-activated receptor (PPAR) agonist.

2. The method of claim 1, wherein said disease is cystic fibrosis.

3. The method of claim 1, wherein said disease is selected from the group consisting of pancreatitis, chronic obstructive pulmonary disease (COPD), asthma, chronic sinusitis, primary sclerosing cholangitis, bile duct injury, liver disease, and congenital bilateral absence of the vas deferens.

4. The method of claim 1, wherein said PPAR agonist is a PPARγ agonist.

5. The method of claim 4, wherein said PPARγ is a PPARγ1.

6. The method of claim 4, wherein said PPARγ agonist is selected from the group consisting of thiazolidinediones, fluoromethyloxycarbonyl, non-steroidal anti-inflammatory drugs, and anti-oxidants.

7. The method of claim 6, wherein said thiazolidinedione is selected from the group consisting of pioglitazone, rosiglitazone, and troglitazone.

8. The method of claim 6, wherein said non-steroidal anti-inflammatory drug is ibuprofen or naprosyn.

9. The method of claim 6, wherein said antioxidant is selected from the group consisting of vitamin E, vitamin C, S-adnenosyl methionine, selenium, beta-carotene, idebenone, cysteine, dithioerythritol, dithionite, dithiothreitol, and pyrosulfite.

10. The method of claim 1, wherein said PPAR agonist is a PPARα agonist.

11. The method of claim 10, wherein said PPARα agonist is selected from the group consisting of DHA, fibrates, and Wy14643.

12. The method of claim 11, wherein said fibrate is selected from the group consisting of fenofibrate, bezafibrate, and gemfibrozil.

13. The method of claim 1, wherein said PPAR agonist is a PPARδ, agonist.

14. The method of claim 1, wherein said PPAR agonist is a PPARα agonist and said disease is bile duct injury or cystic fibrosis liver disease.

15. The method of claim 1, wherein said mutation is a deletion of F508.

16. A method for treating a disease in a human patient, wherein said patient has a mutation in the CFTR gene and wherein said mutation is associated with said disease, said method comprising administering to said patient a therapeutically effective amount of a PPARα agonist and a therapeutically effective amount of a PPARγ agonist.

17. A method for treating a disease in a human patient, wherein said patient has a mutation in the CFTR gene and wherein said mutation is associated with said disease, said method comprising administering to said patient a therapeutically effective amount of a dual PPARα/PPARγ agonist.

18. A method for treating a disease in a human patient, wherein said patient has a mutation in the CFTR gene and wherein said disease is associated with said mutation, said method comprising administering to said patient a therapeutically effective amount of an antioxidant.

19. The method of claim 18, wherein said antioxidant is a PPARγ inducer.

20. The method of claim 18, wherein said antioxidant is selected from the group consisting of vitamin E, vitamin C, S-adnenosyl methionine, selenium, beta-carotene, idebenone, cysteine, dithioerythritol, dithionite, dithiothreitol, and pyrosulfite.

21. The method of claim 3, wherein said disease is primary sclerosing cholangitis.

22. The method of claim 11, wherein said PPARα agonist is DHA.

23. The method of claim 1, wherein said disease is primary sclerosing cholangitis and wherein said PPAR agonist is DHA.

* * * * *